(12) United States Patent
Guo et al.

(10) Patent No.: US 9,234,002 B2
(45) Date of Patent: Jan. 12, 2016

(54) SMALL PEPTIDE SPECIFIC FOR LUNG CANCER AND APPLICATION THEREOF

(71) Applicant: Guangzhou Peptide Medical Technology Co., Ltd., Guangzhou (CN)

(72) Inventors: Linlang Guo, Guangzhou (CN); Guiping Li, Guangzhou (CN); Zhenzhu Chen, Guangzhou (CN); Yajie Liu, Guangzhou (CN)

(73) Assignee: GUANGZHOU PEPTIDE MEDICAL TECHNOLOGY CO., LTD., Guangzhou (CN)

( * ) Notice: Subject to any disclaimer, the term of this patent is extended or adjusted under 35 U.S.C. 154(b) by 0 days.

(21) Appl. No.: 14/523,986

(22) Filed: Oct. 27, 2014

(65) Prior Publication Data

US 2015/0112043 A1 Apr. 23, 2015

Related U.S. Application Data

(63) Continuation-in-part of application No. PCT/CN2012/076102, filed on May 25, 2012.

(30) Foreign Application Priority Data

Apr. 25, 2012 (CN) .......................... 2012 1 0123590
Apr. 25, 2012 (CN) .......................... 2012 1 0123601

(51) Int. Cl.
*C07K 7/06* (2006.01)
*A61K 51/08* (2006.01)
*C07K 1/13* (2006.01)

(52) U.S. Cl.
CPC . *C07K 7/06* (2013.01); *A61K 51/08* (2013.01); *A61K 51/082* (2013.01); *C07K 1/13* (2013.01)

(58) Field of Classification Search
CPC .......... A61K 51/088; A61K 47/48246; A61K 49/221; A61K 51/0474; A61K 49/14; A61K 47/48238; A61K 38/08; C07K 7/64; C07K 7/06; C07K 1/13; C07K 17/06
See application file for complete search history.

(56) References Cited

FOREIGN PATENT DOCUMENTS

CN 101486754 A * 7/2009 ............... C07K 7/06

OTHER PUBLICATIONS

Aleanzi et al. Celiac disease: antibody recognition against native and selectively deamidated gliadin peptides. Clin Chem. Nov. 2001;47(11):2023-8.*
Askoxylakis et al. Characterization and development of a peptide (p. 160) with affinity for neuroblastoma cells. J Nucl Med 2006; 47:981-988.*
Betts et al. Bioinformatics for Geneticists. 2003. Chapter 14: 289-316. ISBNs: 0-470-84393-4.*
Nock et al. Potent Bombesin-like Peptides for GRP-Receptor Targeting of Tumors with 99mTc: A Preclinical Study. J. Med. Chem. 2005, 48, 100-110.*
Guo et al. A novel Specific Small Molecule Peptide for Non-small Cell Lung Cancer Cell A549. Progress in biochemistry and Biophysics. 2007; 34(10):1080-1085.*

* cited by examiner

*Primary Examiner* — Karlheinz R Skowronek
*Assistant Examiner* — Jia-Hai Lee
(74) *Attorney, Agent, or Firm* — Matthias Scholl, PC; Matthias Scholl

(57) ABSTRACT

A peptide including 8 amino acids having a sequence of cNGEGQQc, where c represents d-cysteine (Cys), N represents L-Asparagine (Asn), G represents L-Glycine (Gly), E represents L-Glutamic acid (Glu), and Q represents L-Glutamine (Gln).

4 Claims, 18 Drawing Sheets

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Fully synthetic peptide

<400> SEQUENCE: 1

Cys Asn Gly Glu Gly Gln Gln Cys
1               5

SMALL PEPTIDE SPECIFIC FOR LUNG CANCER AND APPLICATION THEREOF

CROSS-REFERENCE TO RELATED APPLICATIONS

This application is a continuation-in-part of International Patent Application No. PCT/CN2012/076102 with an international filing date of May 25, 2012, designating the United States, now pending, and further claims priority benefits to Chinese Patent Application No. 201210123601.2 filed Apr. 25, 2012, and to Chinese Patent Application No. 201210123590.8 filed Apr. 25, 2012. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18$^{th}$ Floor, Cambridge, Mass. 02142.

BACKGROUND OF THE INVENTION

1. Field of the Invention

The invention relates to a small peptide and specifically to imaging and treatment of a non-small cell lung cancer.

2. Description of the Related Art

Lung cancer is one of the most common cancers and is the leading cause of cancer death worldwide. Non-small cell lung cancer (NSCLC) accounts for approximately 85% of all lung cancers. There are three types of cancer that are considered NSCLC including adenocarcinoma, squamous cell carcinoma (SCC), and large cell undifferentiated carcinoma. Approximately three quarters of patients with lung cancer have an advanced stage of tumor at the time of diagnosis. The most recent statistics show the overall five-year survival of lung cancer is about 10% to 16% in the United States, Europe and China after diagnosis. The survival of lung cancer is heavily dependent on early diagnosis. For example, 5-year survival of Stage IA/B lung cancer is approximately 70% and for Stage IIA/B disease is in the range of 50% when patients are eligible to receive surgery. Therefore, early detection improves apparent survival of lung cancer patients, even if mortality remains unchanged.

Globally, imaging such as PET/CT or single-photon emission computed tomography (SPECT) remains the most effective methods for lung cancer detection. Unfortunately, these current scanning modalities are not sufficiently sensitive or specific to clearly determinate between benign and malignant solitary pulmonary nodules. The false-positive imaging may happen in inflammation (e.g., pneumonia and active tuberculosis) and granulomatous disease (e.g., sarcoidosis and Wegener's granulomatosis) because these pulmonary nodules have the same high uptake of FDG as malignancy. Meanwhile, limitations of PET/CT for evaluating lung nodules are a reduction in specificity and increased false negatives in very small tumors or those with low FDG uptake (e.g., bronchoalveolar carcinomas) (Maffione A M, et al. J Nucl Med. 2014; 55: 983-988). SPECT is widely available, has lower costs than PET/CT, and does not require the presence of a cyclotron adjacent to the hospital. Encouraging results have been obtained with SPECT scanning using sestamibi to detect primary lung malignancies and to perform mediastinal staging with a higher diagnostic accuracy higher than chest CTs. However, the main difficulty is related to the limited spatial resolution of SPECT. To overcome the limited resolution of SPECT, many investigators are working on developing novel sensitive and specific radiotracers for SPECT.

Application for molecularly targeted agents in a non-small cell lung cancer (NSCLC) has witnessed swift evolution in the last decade. These targeted anticancer agents promise more efficient and less toxic side effects for patients as compared with common chemotherapeutic agents. The EGF receptor (EGFR) is therapeutically targeted by antibodies (Cetuximab) and small molecules (Iressa, erlotinib) in solid tumors including lung, colorectal, and breast cancer. However, a small percentage of patients (21%) with an EGFR mutation have higher response rates and all patients eventually develop resistance. Another promising approach has been obtained in radioimmunotherapy (RIT) for the treatment of B-cell non-Hodgkin's lymphoma with yttrium-90 ($^{90}$Y)-ibritumomabtiuxetan (Zevalin) and iodine-131 ($^{131}$I)-tositumomab (Bexxar). $^{131}$I-chTNT is the first approved clinical trial radiolabeled antibody for the treatment of solid tumors including lung cancer, glioblastoma, head and neck cancer, colorectal carcinoma, hepatocellular carcinoma, etc. However, the response rate (ORR) was only 33% in non-small-cell lung cancer patients (Chen S, et al. J Clin Oncol. 2005; 23: 1538-47). $^{131}$I-chTNT was iodine-131-labeled recombinant human and mouse chimeric TNT antibody and has potential allergen. It is, therefore, essential to seek more effective and less toxic modes of therapy for advanced lung cancer.

SUMMARY OF THE INVENTION

In certain embodiments, this invention is directed to a peptide comprising 8 amino acids with the sequence of cXGXGXXc (SEQ ID NO. 2) for NSCLC cells. c represents d-cysteine (Cys) on the N- and C-termini providing intramolecular cyclization by disulfide bonding. G represents L-Glycine (Gly). X is selected from any one of the 20 standard amino acids.

In certain preferred embodiments, this invention is directed to a pharmaceutical composition comprising a peptide with the sequence cNGEGQQc (SEQ ID NO. 1) as a pharmaceutically acceptable carrier of the compound of formula. c represents d-cysteine (Cys). N represents L-Asparagine (Asn). G represents L-Glycine (Gly). E represents L-Glutamic acid (Glu). Q represents L-Glutamine (Gln).

In other aspects, the invention is directed to methods of molecular imaging probe for non-small cell lung cancer. The peptide stated above was labeled with Technetium-99m ($^{99m}$Tc) to generate $^{99m}$Tc-cNGEGQQc. For evaluation as a SPECT imaging agent, the labeled compounds were then tested for the imaging of H1975 (adenocarcinoma) and L78 (squamous carcinoma) xenograft tumors in mice.

In other aspects, the invention is directed to methods of targeting radiotherapeutic agent for non-small cell lung cancer. The peptide stated above was labeled with iodine-131 to generate $^{131}$I-cNGEGQQc. The labeled peptides were then evaluated in mice for the therapeutic effects of H1975 and L78 xenograft tumors.

This invention relates to a novel peptide comprising 8 animo acids with the sequence of cNGEGQQc that specifically recognizes cells of human NSCLC. Further, this invention relates to a pharmaceutically targeted carrier for delivery of imaging agents and therapeutics to NSCLC. More specifically, the peptide of this invention is applied to combine $^{99m}$Tc as specific imaging probe and to combine $^{131}$I as targeting radiotherapeutic agent in the imaging and treatment of non-small cell lung cancer.

Peptide of this invention may be used in combination with known imaging agents. The imaging agents comprise $^{99m}$Tc, $^{111}$In, $^{18}$F-FDG, $^{68}$Ga, $^{64}$Cu.

Generally, molecular imaging probe is prepared according to the following manner.

First, the peptide of the invention was synthesized commercially in their native L configurations with an amino hexyl linker on the terminal amine for conjugation and provided at 97% purity as determined by reversed-phase high-performance liquid chromatography (RP-HPLC).

The peptide prepared above was then conjugated to a chelator of S-acetyl-mercaptoacetyltriglycine (MAG$_3$) to produce peptide-MAG$_3$ complex and subsequently labeled by $^{99m}$Tc. For conjugation of the peptide with $^{99m}$Tc, the following methods were described by Wang Y et al (Wang Y, et al. Nat Protoc. 2006; 1: 1477-80).

Synthesis of SATA. S-acetyl mercaptoacetic acid was synthesised under optimum conditions from mercaptoacetic acid and acetic anhydride. SATA was further obtained when S-acetyl mercaptoacetic acid was reacted with the same molar equivalent of NHS ester via DCC.

Synthesis and Labeling of peptide-MAG3. Peptide was prepared by solid-phase synthesis and conjugated to MAG3. The peptide-MAG3 (10 mL of a mg/mL solution) were labeled with technetium-99m using labeling buffer (0.25 mol/L Sodium Bicarbonate, 0.125 mol/L ammonium acetate, 0.18 mol/L ammonium hydroxide, 1:1:1). The reaction was induced by heating the mixture to 100° C. for 20 min.

Peptide of this invention may be used in combination with known radiotherapeutic agents. The radiotherapeutic agents comprise $^{131}$I and $^{125}$I.

Generally, radiotherapeutic agent is prepared according to the following manner.

The N-terminal of peptide prepared above was coupled to C-terminal of tyrosine by condensation reaction with EDC-HCI (1-ethyl-(3-dimethylaminopropyl) carbodiimide hydrochloride amine). The reaction time was 2 hours at room temperature.

The complex was subsequently reacted with $^{131}$I (37 MBq/20 µl) by adding chloramine T (final concentration 0.9 µg/µl) and stopped by adding 45 µl (4 µg/µl) of sodium thiosulfate. The reaction time was 2 minutes at room temperature.

DETAILED DESCRIPTION OF THE EMBODIMENTS

The following experimental examples are provided in order to demonstrate and further illustrate the invention in detail. These examples are intended merely to illustrate the disclosed methods and products. However, the examples should not be construed as limiting in any manner.

Example 1

Synthesis of cNGEGQQc (SEQ 1N NO. 1) Using Solid-Phase Peptide Synthesis

First, one gram of the resin beads with NH$_2$ functional groups was swollen in dimethylformamide (DMF) and washed with water. After water was drained, d-cysteine and N,N'-diisopropyl carbodiimide were added to the beads. The reaction time was 2 hours at room temperature. Next, beads were washed with DMF for five times. A solution of 20% (v/v) piperidine in DMF was added to the beads. The reaction mixture was stirred for 15 min to allow the Fmoc deprotection.

The process for deprotection and coupling was then repeated until the last amino acid in the sequence was successfully coupled. After the beads were washed with 25% (v/v) trifluoroacetic acid once and distilled water three times, peptides were cleaved from the resin with anhydrous hydrogen fluoride (HF). A disulfide bond in peptides was formed between two cysteines by oxidation with iodine in 30% (v/v) acetic acid. The cleaved peptides were purified using gel filtration on Sephadex G-15 column, followed by high-performance liquid chromatographic purification (HPLC). The purified peptides showed a single major peak by RP-HPLC analysis.

Example 2

Preparation of Molecular Probe $^{99m}$Tc-cNGEGQQc for Imaging Lung Cancer

Figure 1:
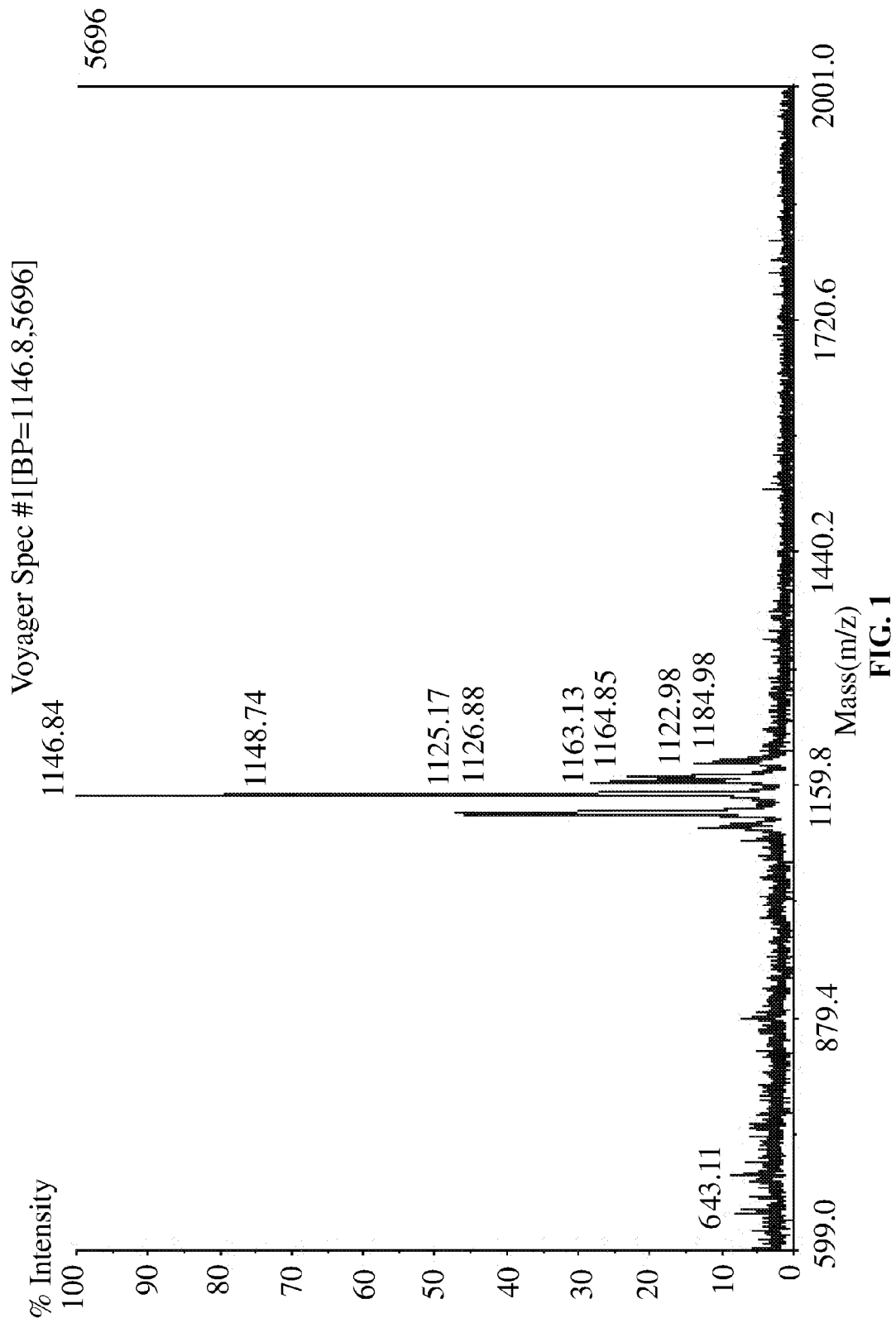
FIG. 1 shows mass spectrometry (MS) analysis of cNGEGQQc-MAG3.
Figure 2:
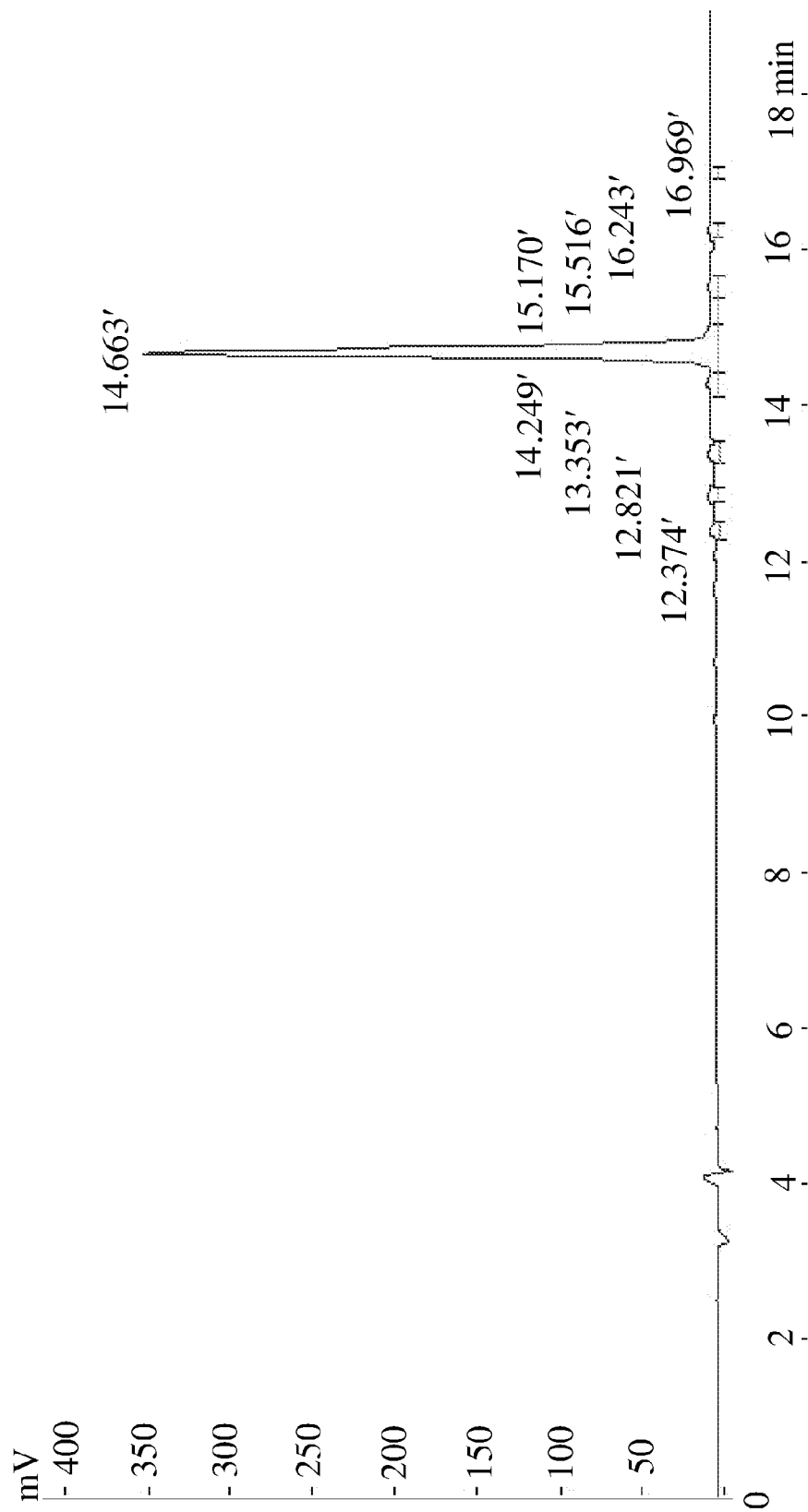
FIG. 2 shows high performance liquid chromatography (HPLC) analysis of cNGEGQQc-MAG3.

The purified peptides above were conjugated to S-acetyl-mercaptoacetyltriglycine (MAG$_3$) to produce peptide-MAG$_3$ complex. The theoretical molecular weight of the peptide is 1125.05 Da, while accurate molecular weight of the purified peptides was determined to be 1146.84 Da by mass spectrometry (FIG. 1). The purity of peptides was monitored as 96% by HPLC (FIG. 2). For conjugation of the peptide-MAG$_3$ complex, the procedure was performed according to the following manner.

1) Synthesis of SATA. S-acetyl mercaptoacetic acid was synthesized from mercaptoacetic acid and acetic anhydride with 1:1.1 molar ratios at room temperature for 4 days. The high purity complex was obtained under reduced pressure (115-125° C., 2-3 mmHg). Both S-acetyl mercaptoacetic acid (75 mmol) and NHS (75 mmol) were dissolved in 150 mL of dioxane. After cooling on ice, dicyclohexylcarbodiimide (DCC) (75 mmol) in 10 mL of THF was added and the reaction mixture stirred for 16 h. The precipitated dicyclohexylurea was removed by filtration and the solvent evaporated to dryness under vacuum. The residue was crystallized twice with isopropanol.

2) Synthesis of peptide cNGEGQQc-MAG3. Peptide cNGEGQQc was prepared by conventional solid-phase synthesis. During the synthesis, three glycines were coupled to the N-terminus of peptide. A one-fold molar excess of SATA was added into peptide solution with 7-fold molar excess of 3mDIEA (diisopropylethylamine) and 3-fold molar excess of HBTU (O-Benzotriazole-N,N,N',N'-tetramethyl-uronium-hexafluoro-phosphate) and 3-fold molar excess of HOBT (1-hydroxybenzotriazole). The mixture was incubated at room temperature for 1 h. The reaction was done when Ninhydrin reaction showed in yellow colouration. After completing synthesis, the peptide resin was washed with NMP (N-methylpyrrolidone) and DCM (dichloromethane) alternately, removed from the column and dried in vacuo. The peptides were cleaved from the resins by treatment with mixture solution (1 mL of ethanedithiol, 1 mL of thioanisole, 0.5 g of phenol, 0.4 mL of H$_2$O and 0.1 mL of triisopropylsilyl) for 7 h. The crude complex was precipitated with diethyl ether 4 times and separated by centrifugation and freeze dried. Purified complex was characterized by analytical HPLC. Conjugation of MAG3 using this protocol was done directly during the synthesis of cNGEGQQc.

Labeling cNGEGQQc-MAG$_3$ with $^{99m}$Tc was performed according to the reference (Winnard P, et al. Nucl Med Biol, 1997; 24: 425-432) with minor improvements. The conjugated peptides cNGEGQQc-MAG$_3$ (20 μg) were labeled with fresh $^{99m}$TcO4$^-$ solution (37 MBq) using labeling buffer (0.25 mol/L of Sodium Bicarbonate, 0.125 mol/L of ammonium acetate and 0.18 mol/L of ammonium hydroxide). The reaction was incubated at 100° C. for 20 min.

We summarized the 5 important factors in the 4 different conditions for labeling peptide with $^{99m}$Tc (Table 1). The orthogonal design was carried out to optimize the experimental conditions for labeling (Table 2). The optimal labeling conditions by orthogonal design were as follows: final concentration of potassium sodium tartrate turn chelator of 3.5 μg/μL, 5 μg/μL of stannous tartrate and reaction conditions at pH 7.6 and 25° C. for 30 min.

TABLE 1

Important factors for labeling peptide

| Level | Temperature (° C.) | Time (min) | pH | Potassium sodium tartrate (μg/μL) | Stannous tartrate (μg/μL) |
|---|---|---|---|---|---|
| 1 | 25 | 10 | 2.0 | 0.5 | 0.25 |
| 2 | 37 | 20 | 4.0 | 1 | 1 |
| 3 | 75 | 30 | 7.6 | 3.5 | 5 |
| 4 | 100 | 60 | 10.0 | 10 | 10 |

TABLE 2

Orthogonal design of four factors for labeling peptide

| No | Temperature (° C.) | Time (min) | pH | Potassium sodium tartrate (μg/μL) | Stannous tartrate (μg/μL) | Labeling (%) |
|---|---|---|---|---|---|---|
| 1 | 25 | 10 | 2.0 | 0.5 | 0.25 | 7.50% |
| 2 | 25 | 20 | 4.0 | 1 | 1 | 85.60% |
| 3 | 25 | 30 | 7.6 | 3.5 | 5 | 98.60% |
| 4 | 25 | 60 | 10.0 | 10 | 10 | 89.50% |
| 5 | 37 | 10 | 2.0 | 0.5 | 0.25 | 85.20% |
| 6 | 37 | 20 | 4.0 | 1 | 1 | 89.90% |
| 7 | 37 | 30 | 7.6 | 3.5 | 5 | 98.30% |
| 8 | 37 | 60 | 10.0 | 10 | 10 | 91.50% |
| 9 | 75 | 10 | 2.0 | 0.5 | 0.25 | 85.40% |
| 10 | 75 | 20 | 4.0 | 1 | 1 | 91.50% |
| 11 | 75 | 30 | 7.6 | 3.5 | 5 | 94.80% |
| 12 | 75 | 60 | 10.0 | 10 | 10 | 97.70% |
| 13 | 100 | 10 | 2.0 | 0.5 | 0.25 | 97.60% |
| 14 | 100 | 20 | 4.0 | 1 | 1 | 89.10% |
| 15 | 100 | 30 | 7.6 | 3.5 | 5 | 93.50% |
| 16 | 100 | 60 | 10.0 | 10 | 10 | 10.50% |

Example 3

Labeling Efficiency and Stability of Molecular Probe ($^{99m}$Tc-cNGEGQQc)

Labeling efficiency of molecular probe was determined by paper chromatography. The details were as follow: A drop of the molecular probe was placed on one side of the paper, then dipped into a mixture liquid with ethanol:ammonia:water (2:1:5) (system 1) and acetone (system 2). The separation occurs as the liquid moves along the paper. Take the paper out and dry it when the liquid moves to the other side of paper. Paper was cut into ten equal pieces and put into the tube separately. The radioactivity of each pieces of paper was measured by radioactivity counter and calculated the percentage of radioactivity and labeling rate. (Radioactivity percentage=(radioactivity count/total radioactivity count)×100%) (Labeling rate=radioactive percentage of $^{99m}$Tc-labeled peptides−radioactivity percentage of $^{99m}$Tc). The peptides were labeled using optimal labeling conditions and measured by paper chromatography. The labeling rate of cNGEGQQc using $^{99m}$Tc ranged 84%-95%.

Figure 3:
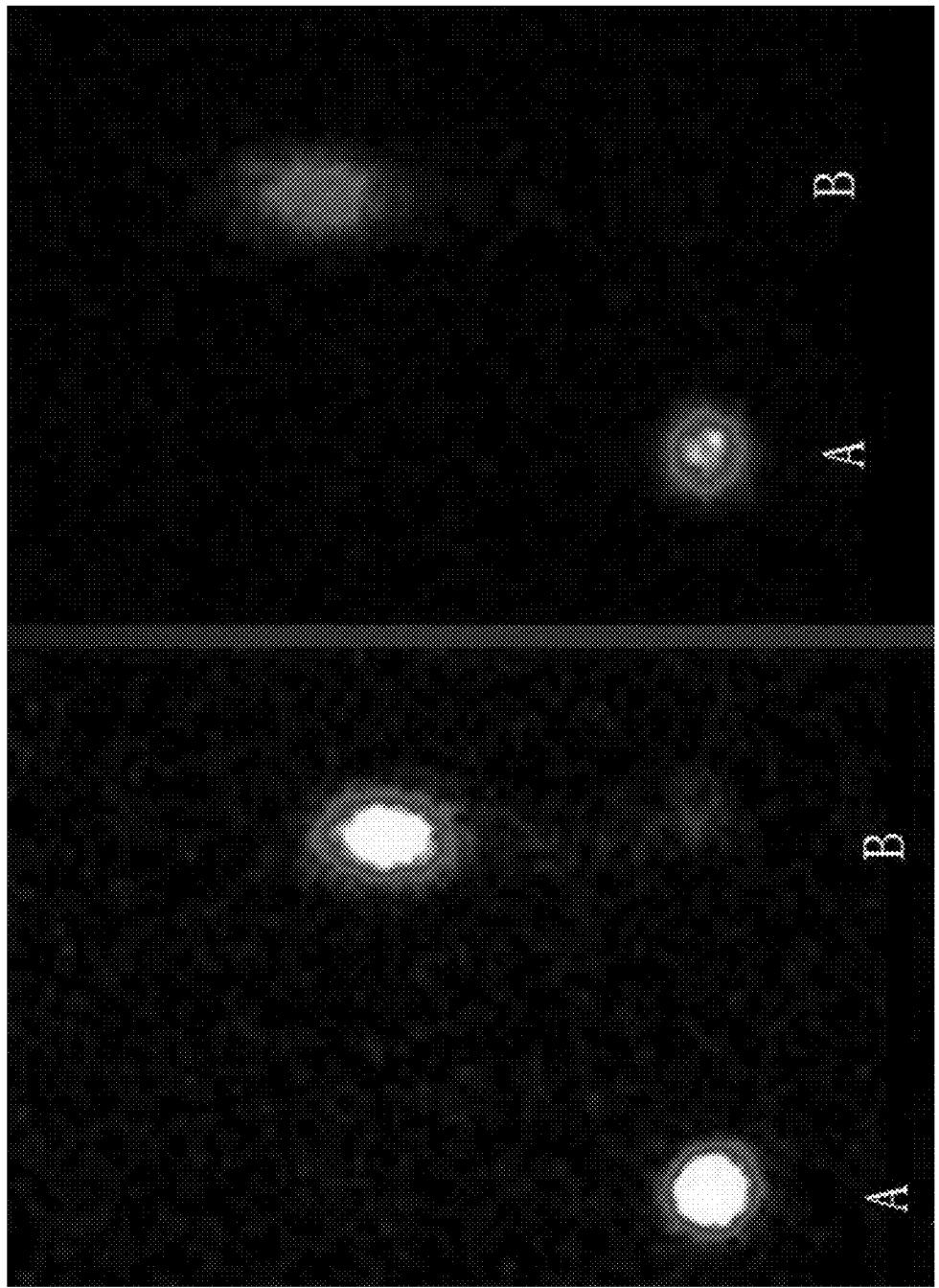
FIG. 3 shows stability testing of molecular imaging probe $^{99m}$Tc-cNGEGQQc by paper chromatography (A. acetone system; B. ammonia/ethanol/water mixture system)

To evaluate the stability of molecular probe in vitro, radiochemical purity was measured using paper chromatography. The formula for radiochemical purity is radioactive percentage of $^{99m}$Tc-labeled peptides (system 1)−radioactivity percentage of $^{99m}$Tc (system 2). After purification with HPLC, the $^{99m}$Tc labeled cNGEGQQc was placed at room temperature for 24 h. The radiochemical purity was 95% at 0 h and 90% at 24 h respectively. The stability of $^{99m}$Tc labeled cNGEGQQc was further estimated in fresh human serum at 37° C. for 24 h. After 24 h incubation, 85% of $^{99m}$Tc labeled cNGEGQQc remained intact in serum. The radiochemical purity was 95% at 0 h and 85% at 24 h respectively. These data suggests that $^{99m}$Tc labeled cNGEGQQc is very stable in vitro (FIG. 3).

Example 4

Biodistribution of Molecular Probe ($^{99m}$Tc-cNGEGQQc) in Animals

Figure 4:
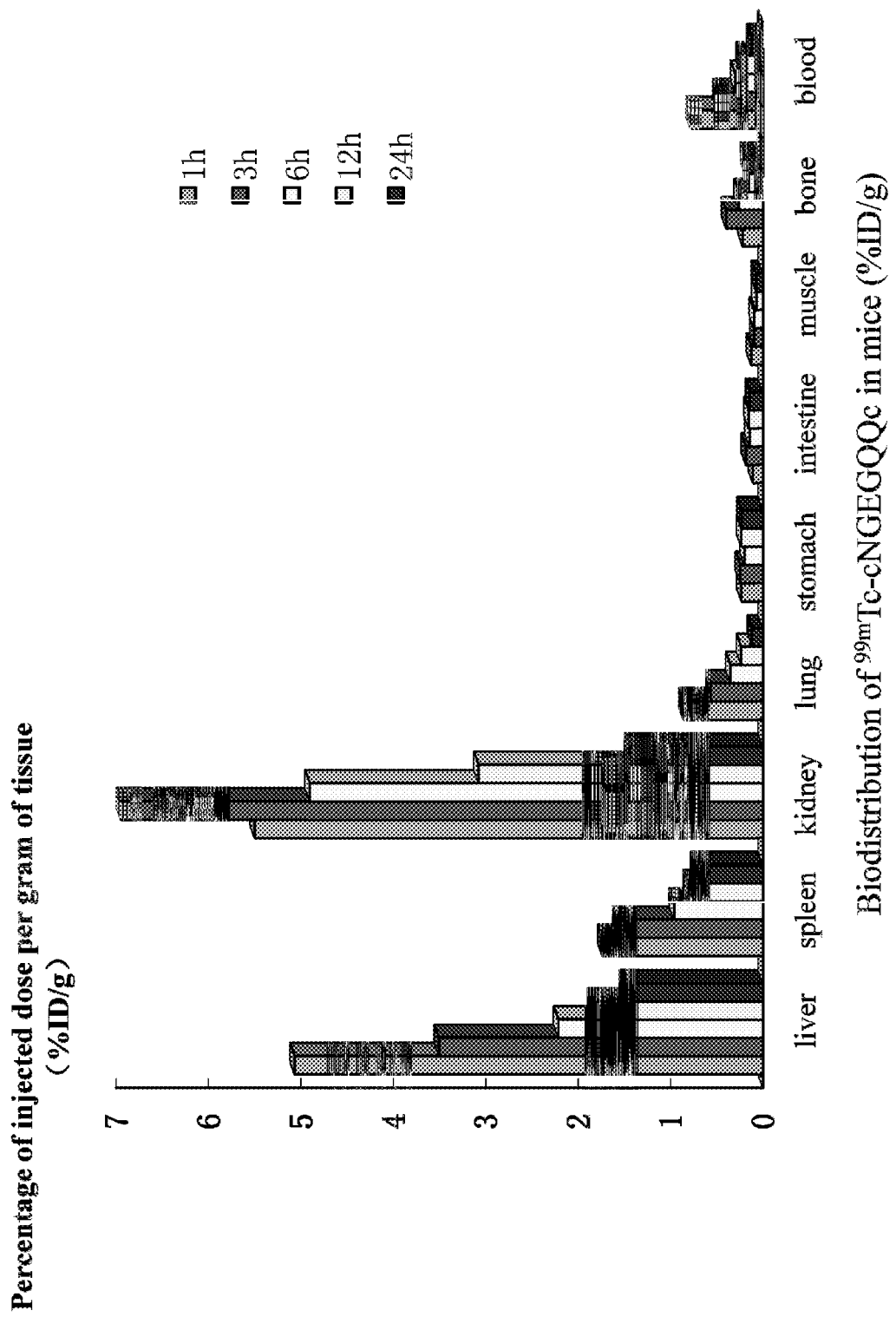
FIG. 4 shows biodistribution of $^{99m}$Tc-cNGEGQQc in mice.
Figure 5:
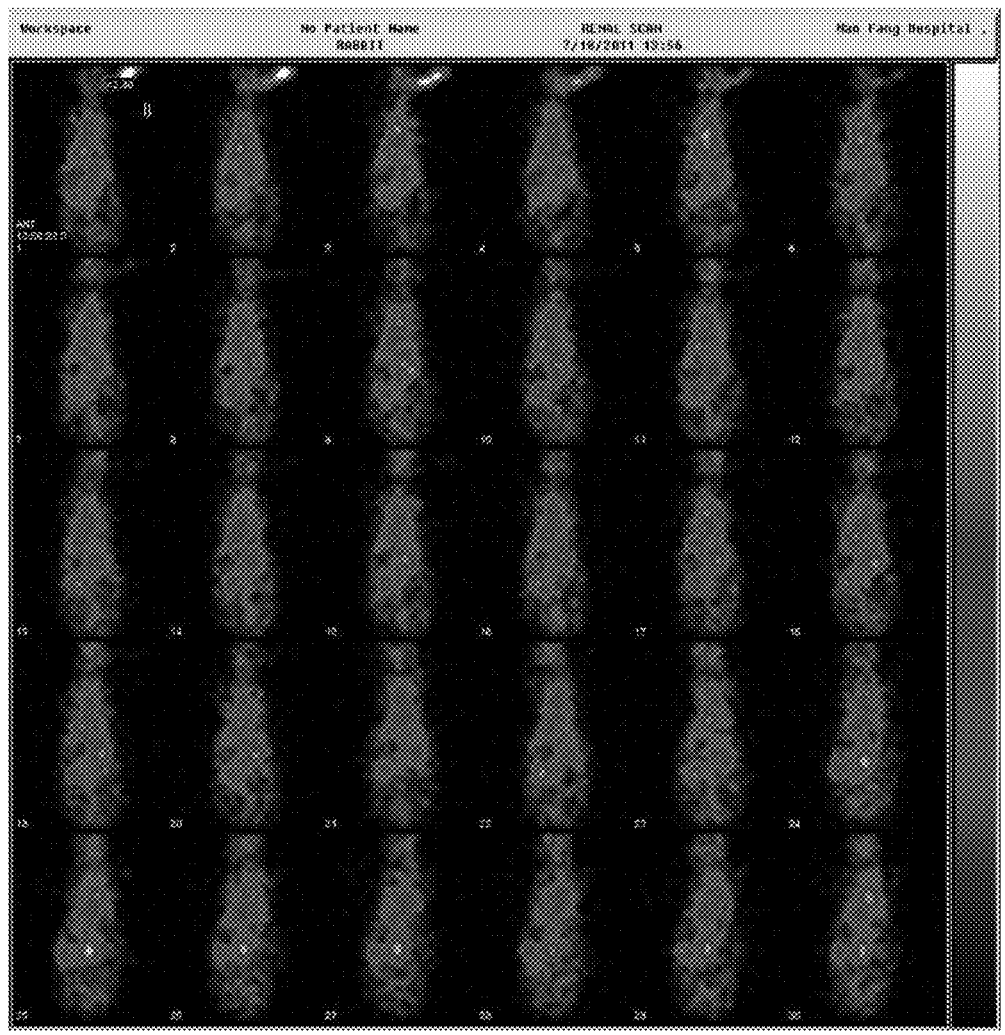
FIG. 5 shows biodistribution of $^{99m}$Tc-cNGEGQQc in rabbits by SPECT scanning for one minute (1 frame/second)
Figure 6:
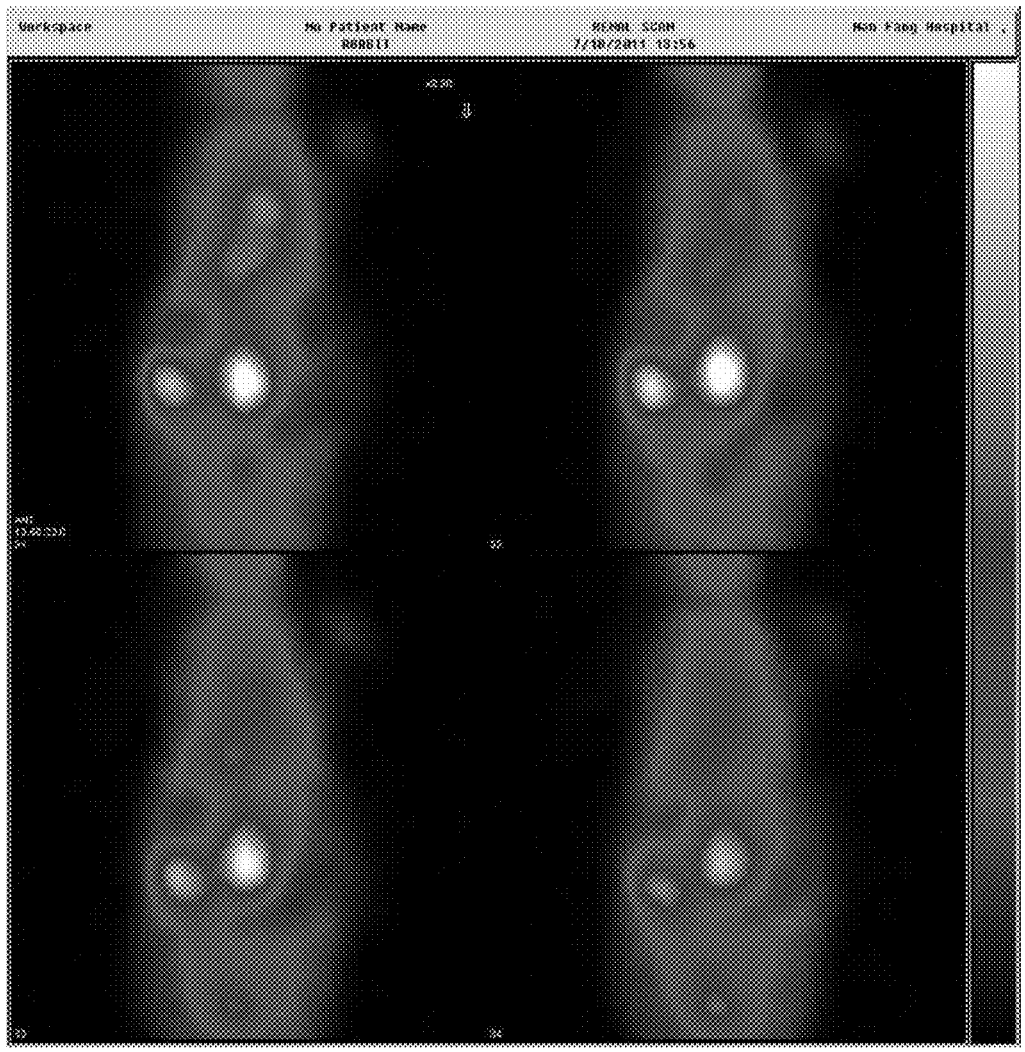
FIG. 6 shows biodistribution of $^{99m}$Tc-cNGEGQQc in rabbits by SPECT scanning for 5 minutes (1 frame/second)
Figure 7:
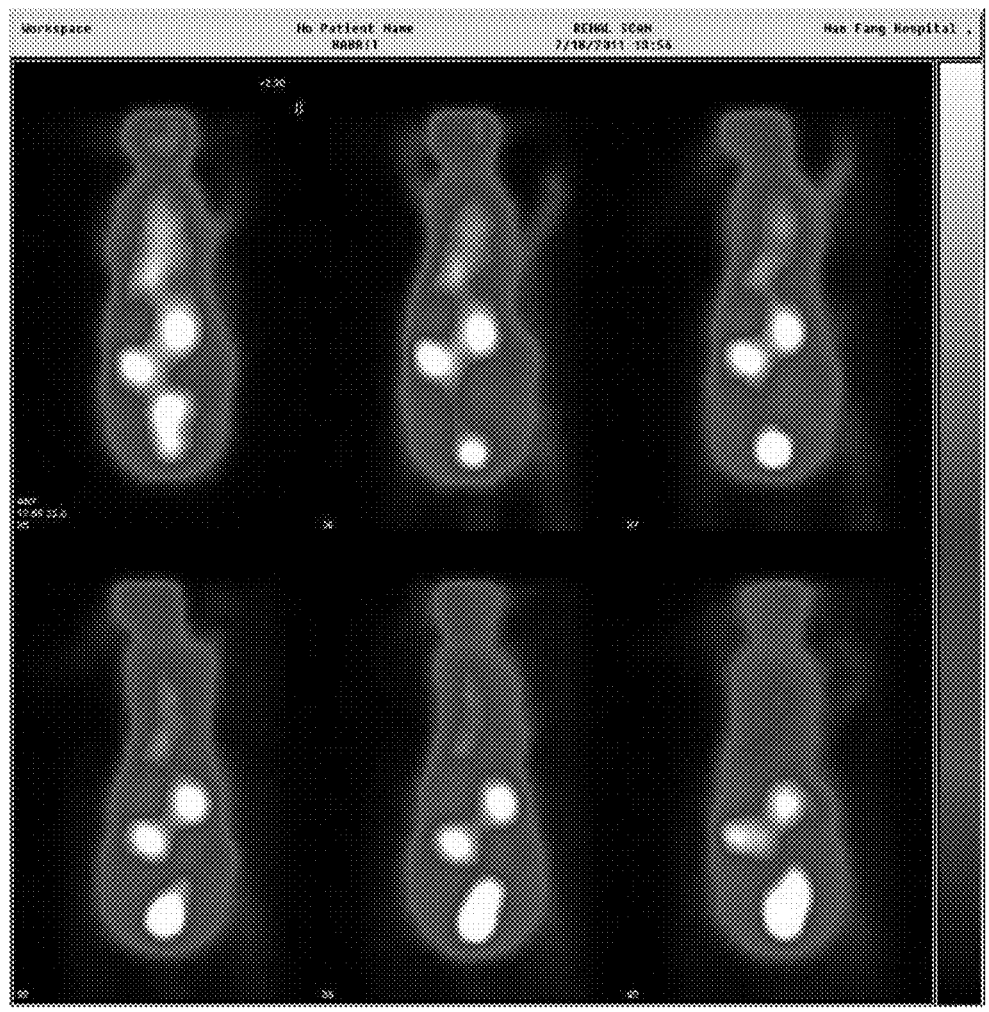
FIG. 7 shows biodistribution of $^{99m}$Tc-cNGEGQQc in rabbits by SPECT scanning for 30 minutes (1 frame/5 minutes)
Figure 8:
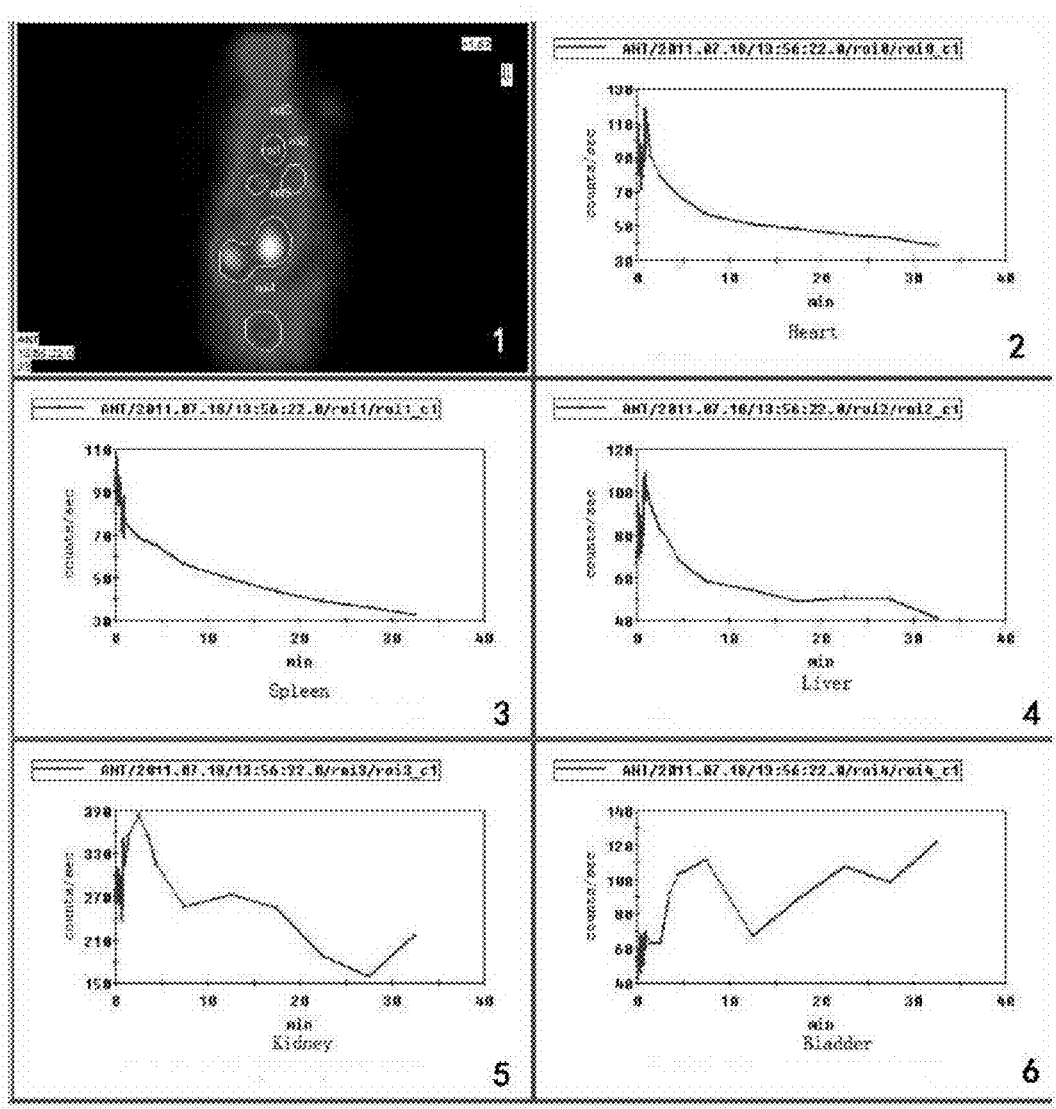
FIG. 8 shows the time-radioactivity curves of heart, liver, spleen, kidney and bladder were measured using the region-of-interest (ROI)-based analysis by injection of $^{99m}$Tc-cNGEGQQc (1. the time-radioactivity curve from ROI analysis after dynamic recording in major organs of normal rats; 2. the time-radioactivity curve of heart; 3. the time-radioactivity curve of spleen; 4 the time-radioactivity curve of liver; 5. the time-radioactivity curve of kidney; 6. the time-radioactivity curve of bladder)
Figure 9:
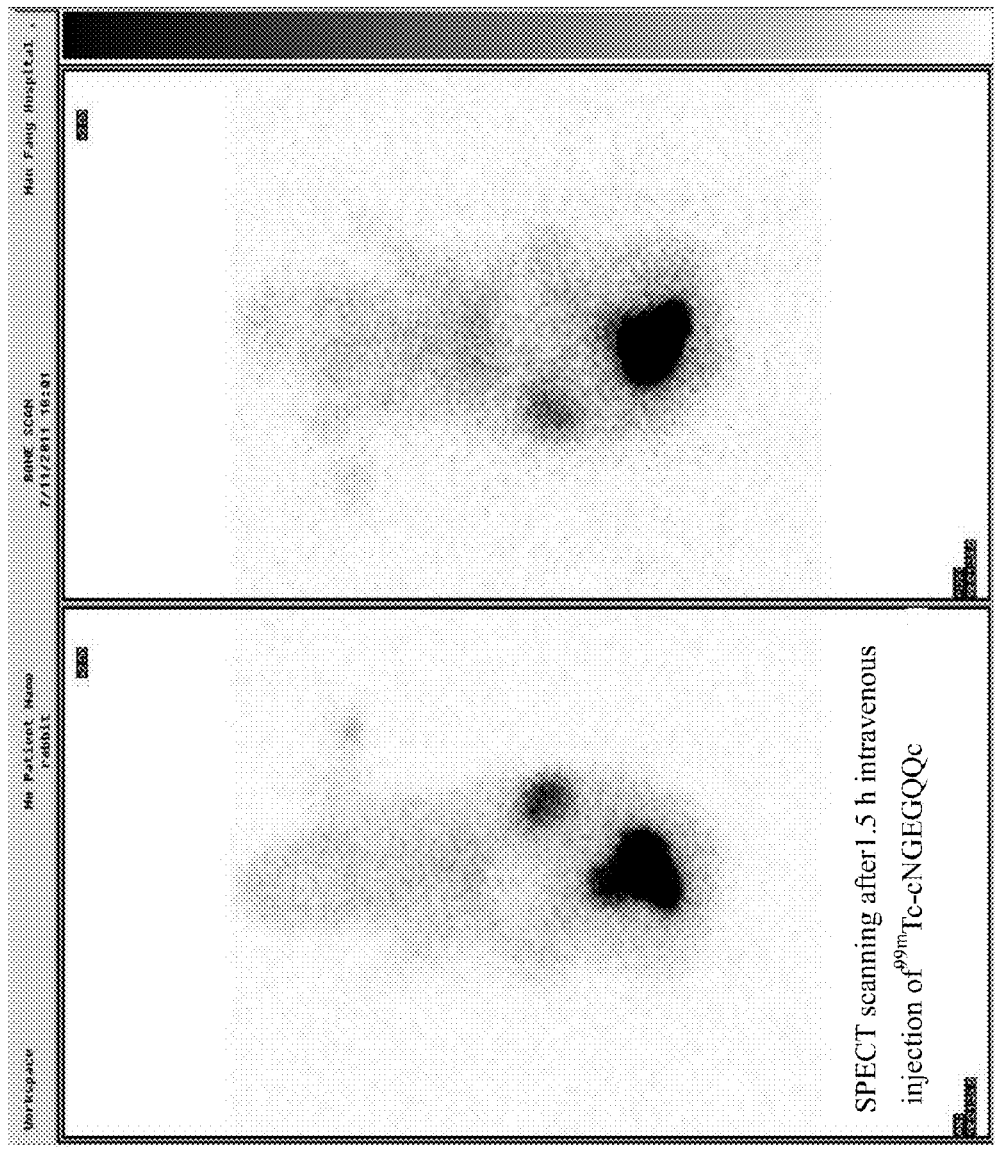
FIG. 9 shows the anterior and rear images were acquired by SPECT scanning after 1.5 h intravenous injection of $^{99m}$Tc-cNGEGQQc.

Fifteen normal Kunming male mice (4-6 weeks old, weight 19-21 g) were injected with 0.1 mL (2.96 MBq) of $^{99m}$Tc-cNGEGQQc via a tail vein respectively. At 1, 3, 6, 12, and 24 h, three animals were anesthetized and sacrificed by cervical dislocation. Whole blood was collected and organs of interest were removed and weighed. The amount of radioactivity in blood and each organ was determined and calculate the percentage of the injected dose per gram of tissue (% ID/g). Subsequently, SPECT (Millennium VG; GE Healthcare) was equipped with a low-energy, high resolution collimator. Images were collected using energy peak centered at 140 KeV, an energy window of 20% and a 128×128 matrix at a magnification of 1.0. The biodistribution $^{99m}$Tc-cNGEGQQc in mice was shown in Table 3 and FIG. 4. SPECT imaging showed that the radioactivity of kidney and liver was significantly higher than that of other organs in healthy mice. The uptake of molecular probe was more and clearance took longer in kidney than that in liver. These results showed that molecular probe mainly excreted by kidneys. During the observation period, the radioactivity of various organs gradually decreased, while the radioactivity of gastrointestinal was relatively stable. It indicated that the stability of molecular probe was excellent and no free $^{99m}$Tc release in vivo. Only little uptake of molecular probe was observed in lung and muscles. Therefore, it will be excellent for imaging of lung cancer patients because good background contrast to tumors.

organs was observed at different time post injection. The posterior dynamic images were analyzed by ROI. The time-radioactivity curves of main organs comprising precordia, liver, spleen, kidney and bladder were obtained respectively by ROI analysis (FIGS. 5-9).

Example 5

Evaluation of Molecular Probe ($^{99m}$Tc-cNGEGQQc) in Mice Bearing Lung Cancer Cells Animal models Two human lung cancer comprising NCI-H1975 (adenocarcinoma) and L78 (squamous carcinoma) and three other cells comprising MCF7 (breast carcinoma), HT-29 (colon carcinoma) and HepG2 (hepatocellular carcinoma) were used in the study. These cell lines were maintained in RPMI 1640 (GIBCO, Mississauga, Canada) supplemented with 10% heat-inactivated calf serum and L-glutamine in an incubator at 37° C. with 5% $CO_2$. Cells were harvested with trypsin/EDTA, washed with PAS twice and re-suspended in free serum culture medium at a concentration of $5\times10^6$ cells/mL. The suspended cells (0.2 mL) were inoculated s.c. into the back of nude mice to establish the cancer models, respectively. There are four nude mice in each group of cancer model. Tumor growth and general states such as mental, diet and weight were monitored periodically. When tumors reached approximately 1 cm in mean diameter, the tumor bearing mice were used in imaging and biodistribution studies.

Imaging of Molecular Probe in Cancer Models

Each tumor-bearing mouse was injected with 0.1 mL (2.96 MBq) of molecular probe via a tail vein respectively and scanned by SPECT. $^{99m}$Tc labeled non-related small peptide cNAQAEQC (SEQ ID NO. 3) was used as a negative control for molecular probe. To monitor the distribution of molecular probe in vivo, images were acquired immediately and at 0.5 h, 1 h, 2 h, 3 h, 5 h, 6 h and 24 h after injection of molecular probe. Imaging at first time point and peak uptake time was also recorded. All these data were used to evaluate the imaging features of molecular probe in lung cancer and other cancer.

TABLE 3

Biodistribution of $^{99m}$Tc-cNGEGQQc in mice (% ID/g)

| Tissues | 1 h | 3 h | 6 h | 12 h | 24 h |
|---|---|---|---|---|---|
| liver | 5.0643 ± 1.3116 | 3.5032 ± 01.4641 | 2.2112 ± 2.8001 | 1.8420 ± 0.5133 | 1.4979 ± 0.0196 |
| spleen | 1.7332 ± 0.1762 | 1.5724 ± 1.0061 | 0.9598 ± 1.1390 | 0.8098 ± 0.0330 | 0.7272 ± 1.1205 |
| kidney | 5.4965 ± 1.1285 | 6.9413 ± 2.12189 | 4.9006 ± 0.7596 | 3.0748 ± 0.3810 | 1.4445 ± 0.2331 |
| lung | 0.8558 ± 0.1760 | 0.5627 ± 0.4336 | 0.3496 ± 0.0457 | 0.2337 ± 0.1501 | 0.1148 ± 0.0137 |
| stomach | 0.2304 ± 0.0708 | 0.2442 ± 0.0857 | 0.1965 ± 0.1023 | 0.2326 ± 0.0691 | 0.2266 ± 0.0162 |
| intestine | 0.1059 ± 0.0296 | 0.1817 ± 0.0737 | 0.1427 ± 0.0550 | 0.1524 ± 0.0150 | 0.1367 ± 0.0256 |
| muscle | 0.1261 ± 0.0818 | 0.0920 ± 0.01511 | 0.0950 ± 0.0257 | 0.0691 ± 0.0185 | 0.0702 ± 0.0007 |
| bone | 0.2165 ± 0.1083 | 0.3969 ± 0.1026 | 0.2590 ± 0.1329 | 0.1524 ± 0.0315 | 0.1886 ± 0.0723 |
| blood | 0.7801 ± 0.3564 | 0.4845 ± 0.1010 | 0.2987 ± 0.1194 | 0.2387 ± 0.0666 | 0.1205 ± 0.0270 |

Biodistribution of Molecular Probe ($^{99m}$Tc-cNGEGQQc) in Rabbits

Figure 10:
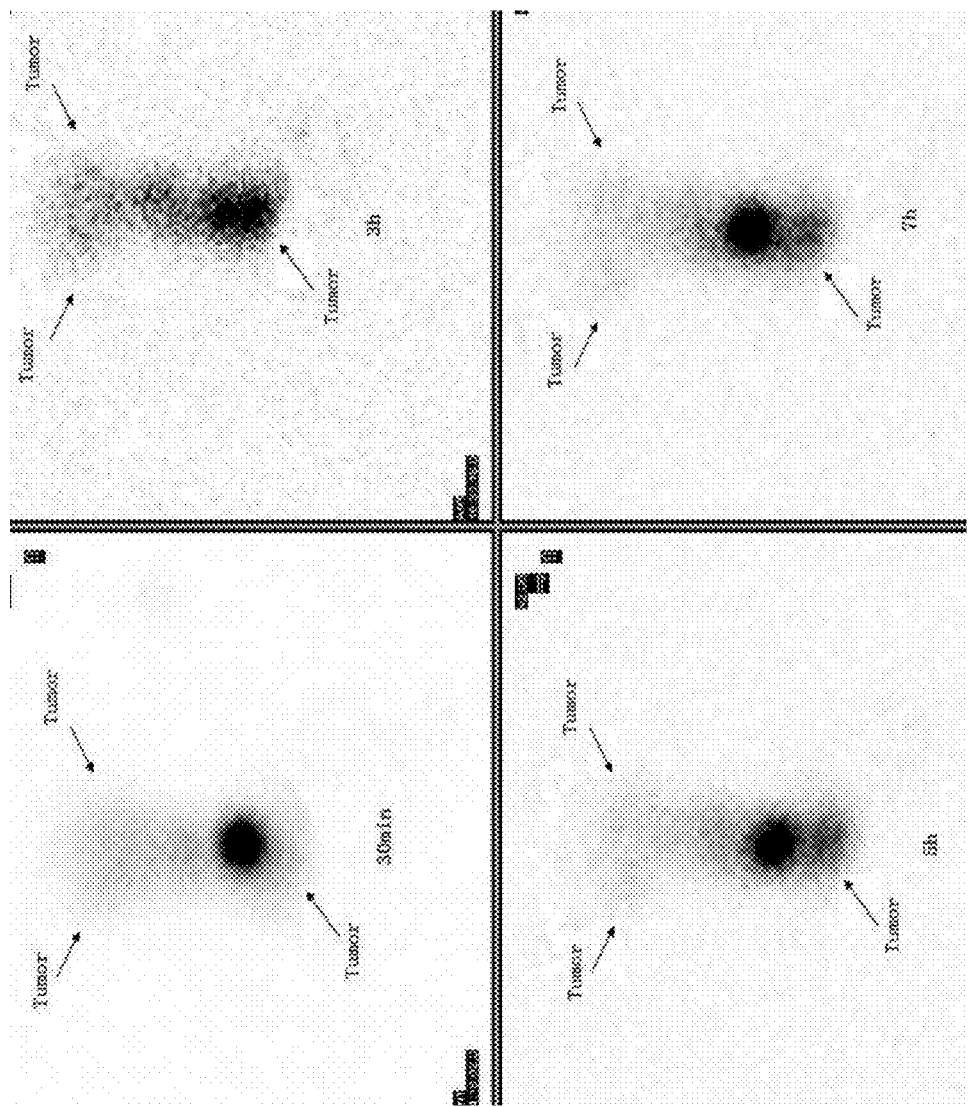
FIG. 10 shows SPECT imaging of mice bearing L78 tumors were obtained after intravenous injection of $^{99m}$Tc-cNGEGQQc at different time (arrows show tracer uptake in the tumors)
Figure 11:
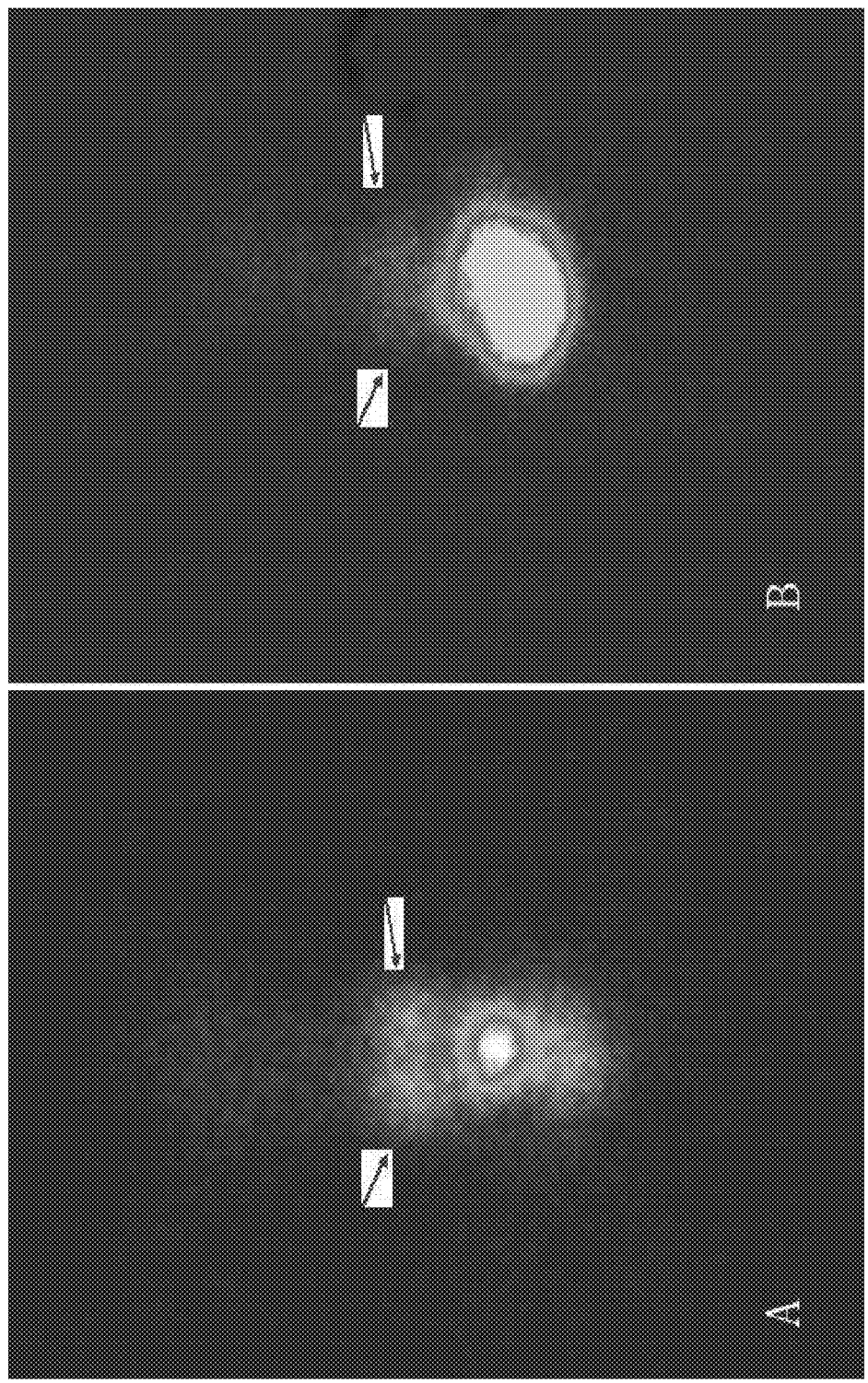
FIG. 11 shows SPECT imaging of mice bearing H1975 tumors were obtained after intravenous injection of $^{99m}$Tc-cNGEGQQc (arrows show tracer uptake in the tumors). (A, after 2 h injection of $^{99m}$Tc-cNGEGQQc; B, after 2 h injection of $^{99m}$Tc-cNAQAEQ) (arrows show tracer uptake in the tumors)

Two of healthy Japanese male white rabbits were fixed in supine position on a wooden experimental stage. We set SPECT collimator on the rabbit thoracic and abdominal to ensure that the whole body of rabbit was within vision field of SPECT imaging. The injectant of molecular probe (0.5 mL/74 MBq) was administered through the ear vein injection. Images were acquired immediately and for the next 60 min at a rate of 1 frame/min after injection of molecular probe, followed a rate of 1 frame/2 min at 90 min, 120 min, 180 min and 240 min. The distribution of molecular probe in animal SPECT imaging of animals injected with molecular probe demonstrated major distribution to the kidneys and bladder and, to a lesser extent, to the liver. Low radioactivity was also observed in the intestine, limbs, head and chest. The increased intense radiotracer activity in bladder was shown while decreased uptake in the tumor (L78). Tumor imaging was vaguely at 30 min after the injection of molecular probe. With the tumor uptake gradually increasing, the image became clear visualization (FIG. 10). FIG. 11 showed that the tumor (H1975) was clearly visualized at 2 h after injection of molecular probe, while the tumor image was blurry after injection of the control probe.

Biodistribution of Molecular Probe ($^{99m}$Tc-cNGEGQQc) in Bearing Tumor Mice

The maximum tumor-specific accumulation occurred at 2 h after injection of molecular probe, while the highest kidney uptake and lowest brain uptake were observed postinjection. The target/non-target (T/NT) ratios were presented in Table 4, molecular probe had the higher tumor-to-brain (10.32) and tumor-to-muscle (4.76) ratios and lower tumor-to-blood ratio (1.46).

TABLE 4

T/NT ratio of $^{99m}$Tc-cNGEGQQc in mice bearing lung cancer (n = 3)

| Tumor/organ | T/NT ratio |
| --- | --- |
| Tumor/liver | 0.47 ± 0.13 |
| Tumor/brain | 10.32 ± 4.26 |
| Tumor/kidney | 0.23 ± 0.18 |
| Tumor/lung | 0.92 ± 0.17 |
| Tumor/heart | 4.43 ± 0.75 |
| Tumor/bone | 1.82 ± 0.84 |
| Tumor/muscle | 4.76 ± 0.79 |
| Tumor/stomach | 1.19 ± 0.11 |
| Tumor/small intestine | 1.11 ± 0.32 |
| Tumor/blood | 1.46 ± 0.26 |

As stated above, the tumor lesions (adenocarcinoma and squamous carcinoma of lung cancer) were clearly visualized after injection of molecular probe. However similar results were not achieved in breast cancer, colon cancer and hepatocellular carcinoma models. Meanwhile, no visual imaging was shown after injection of control probe. These data suggest that the peptide of our invention can be used as a pharmaceutically targeted carrier for delivery of imaging agent $^{99m}$Tc to NSCLC through the blood circulation, and specifically bind to lung cancer cells.

Example 6

Preparation of Radiotherapeutic Agent $^{131}$I-cNGEGQQc for Lung Cancer

Figure 12:
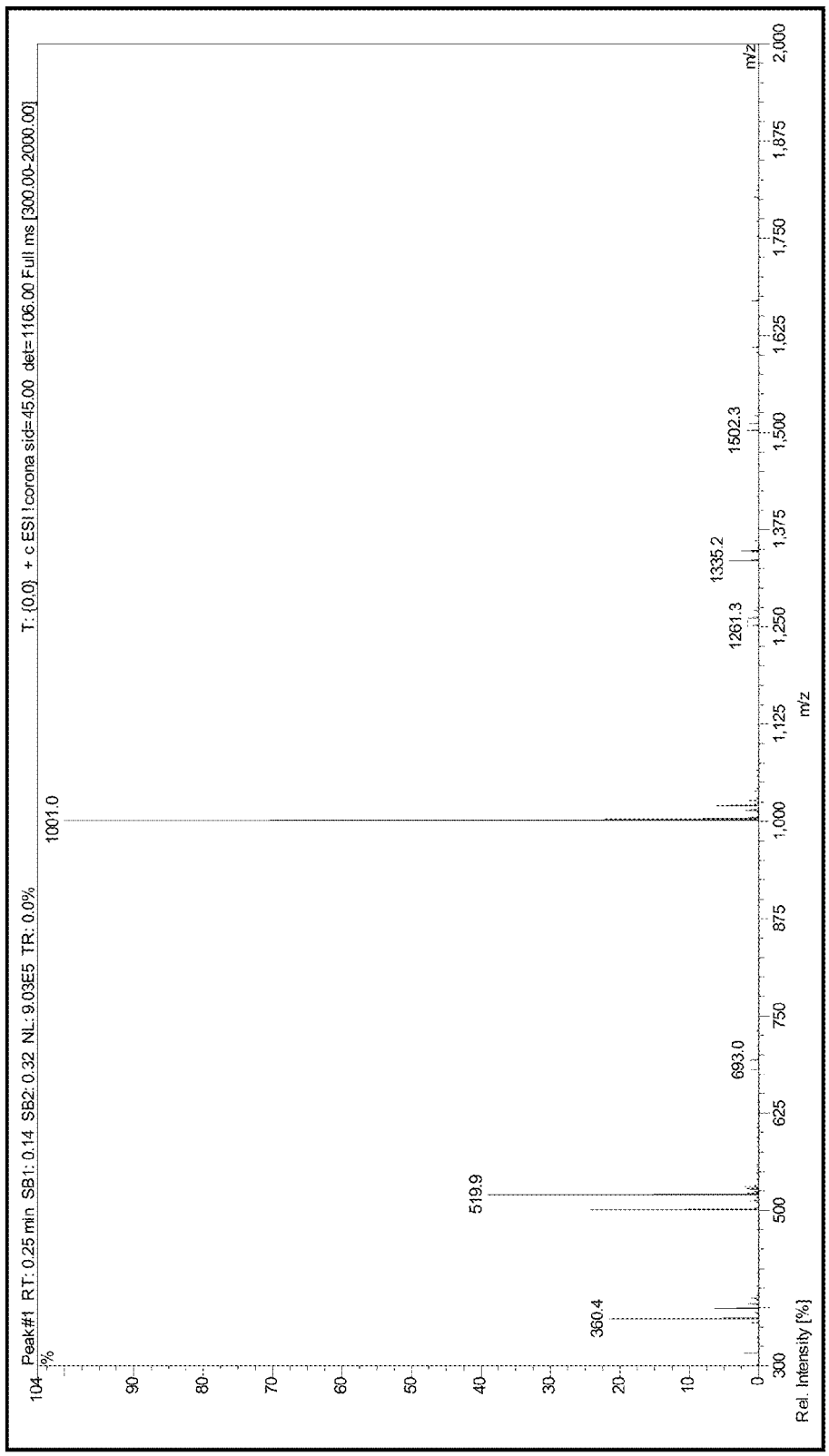
FIG. 12 shows mass spectrometry (MS) analysis of cNGEGQQc-Tyr.

According to the procedure in example 2, cNGEGQQc-Tyr complex was synthesized by condensation reaction between the N-terminal of peptide prepared above and C-terminal of tyrosine with EDC-HCI (1-ethyl-(3-dimethylaminopropyl) carbodiimide hydrochloride amine) (FIG. 12). The molar ratios in reaction mixture were 1:3:3.6. The reaction time was 2 hours at room temperature.

Figure 13:
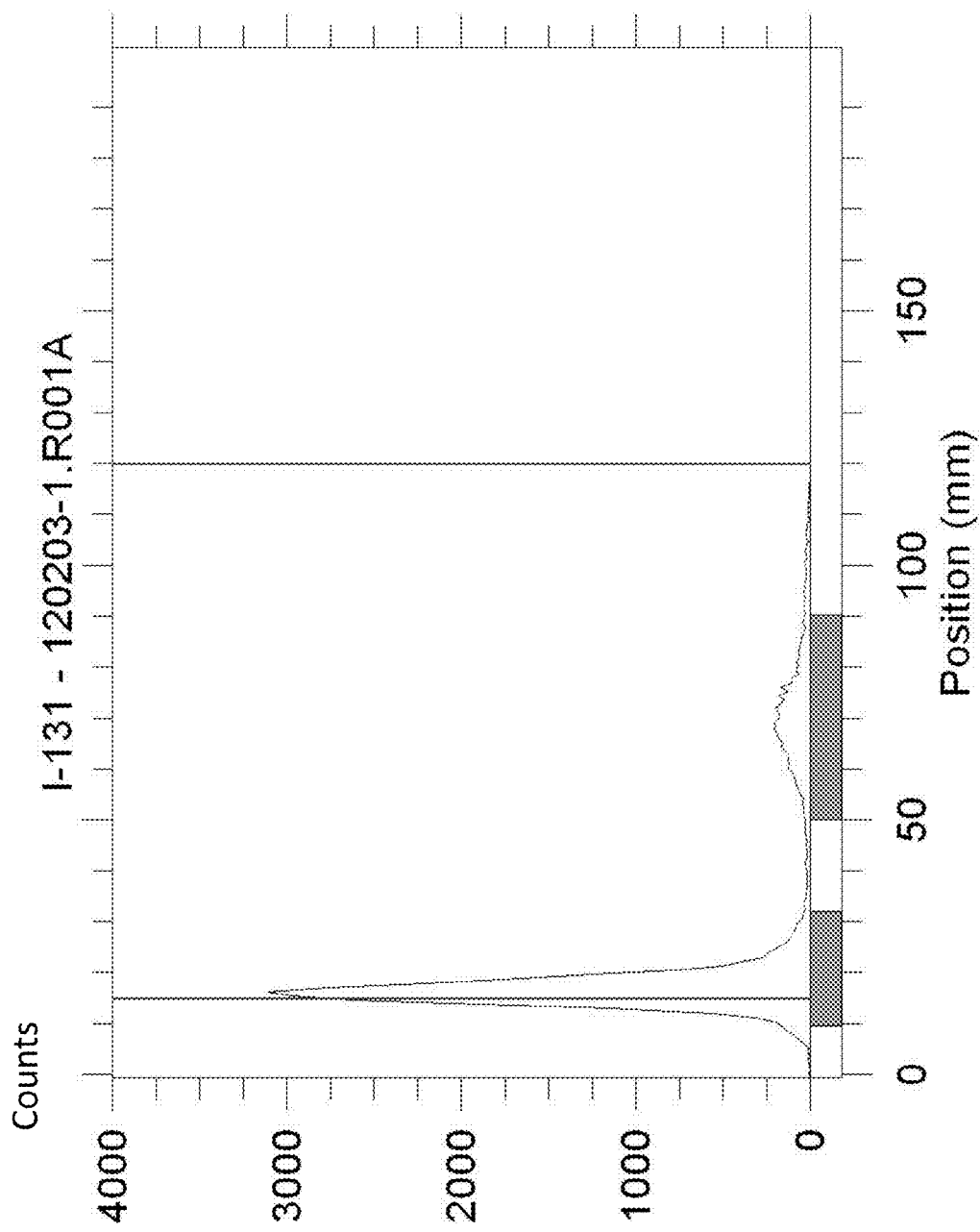
FIG. 13 shows the radiochemical purity (RCP) of $^{131}$I-cNGEGQQc was analyzed by paper chromatography.

For labeling the peptide-Tyr complex with iodine-131 using the chloramine-T method (Yu M, et al. Ann Nucl Med. 2010; 24: 13-9), the procedure was performed according to the following manner Peptide-Tyr complex (50 µg) was dissolved in 50 µl of PBS buffer (0.5M, pH=6.8), then was added to 20 µl of $^{131}$I (37 MBq), followed by 30 µl of chloramine-T (3 µg/µl) (final concentration 0.9 µg/µl). The component was mixed by a shaker for 2 min and the reaction was terminated by adding 45 µl of sodium thiosulfate (4 µg/µl). The reaction mixture was finally added 200 µl of PBS buffer (0.5M, pH=7.4). The peptides were determined by paper chromatography. A drop of the labeled peptides were placed on the paper, then dipped into a mixture liquid with n-butanol:ethanol:ammonia (5:1:2). Labeling efficiency of the labeled peptides was measured using radioactive thin-layer scanner. The labeled peptides were purified using gel filtration on Sephadex G-25 column. The radiochemical purity of purified peptides was measured using paper chromatography (FIG. 13).

The preparation and purification of labeled peptide by Sephadex G25 were as follow: 1 g of Sephadex (dextran gel) 25 were soaked in PBS (pH=7.4) for 24 h. The fine particles were removed by gently shaking. After the Sephadex G25 was completely hydrated, pumping decompression was used to remove the air bubbles. Sephadex G25 was then added into a glass chromatography tube. PBS (pH=7.4) and BSA (20 mg dissolved in 1 mL of PBS) were added into the tube separately. After washing with PBS (pH=7.4), the reaction solution was filtered through the column. The eluate was monitored by absorbance at 280 nm and added appropriate amount of BSA and NaN$_3$, followed by lyophilizing and aliquoting for future use.

Example 7

Figure 14:
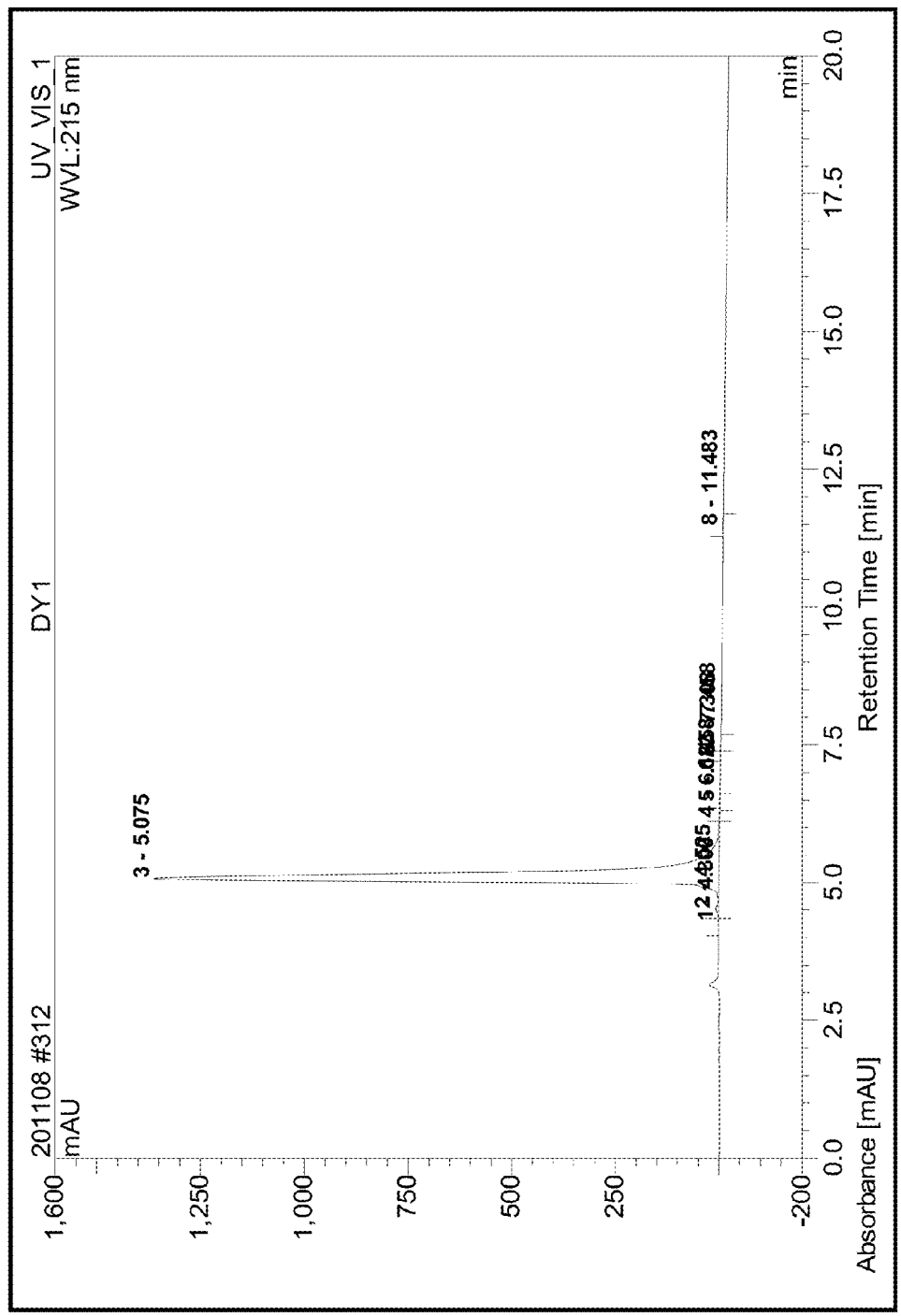
FIG. 14 shows radiochromatograms of $^{131}$I-cNGEGQQc was analyzed by high performance liquid chromatography (HPLC)

Labeling Efficiency and Stability of Radiotherapeutic Agent ($^{131}$I-cNGEGQQc) in Vitro Labeling efficiency of molecular probe was determined by paper chromatography. The details were as follow: A drop of the molecular probe was placed on one side of the paper, then dipped into a mixture liquid with n-butanol:ethanol:ammonia (5:1:2). The separation occurs as the liquid moves along the paper. Take the paper out and dry it when the liquid moves to the other side of paper. Paper was cut into ten equal pieces and put into the tube separately. The radioactivity of each pieces of paper was measured by radioactivity counter and calculated labeling rate (radioactivity peaks of unpurified labeled peptide/sum of each radioactivity peak×100%) and radiochemical purity (radioactivity peaks of purified labeled peptide/sum of each radioactivity peak×100%). Rf of $^{131}$I-labeled peptide was 0-0.1 and Rf of free $^{131}$I was 0.4-0.6 and 0.9-1.0. The optimal conditions for labeling cNGEGQQc with $^{131}$I were as follows: The best peptides/chloramine-T weight ratio was 1:1.8. Reaction conditions were at pH 7.4 and 20° C. for 2 min. The labeling rate of peptides using $^{131}$I in the optimal conditions was over 90%. FIG. 14 present HPLC radiochromatograms of $^{131}$I-labeled peptide.

To evaluate the stability of radiotherapeutic agent at room temperature and in fresh human serum for 24 h, radiochemical purity was measured using paper chromatography. After purification with HPLC, the radiochemical purity of $^{131}$I-labeled cNGEGQQc was >90% at room temperature for 24 h. The stability of $^{131}$I-labeled cNGEGQQc was further estimated in fresh human serum at 37° C. for 24 h. After 24 h incubation, 85% of $^{131}$I-labeled cNGEGQQc remained intact in serum. The radiochemical purity was 92.5% at 0 h and 88.2% at 24 h respectively. These data suggests that $^{131}$I-labeled cNGEGQQc is very stable in vitro and satisfactory to support biological evaluation in vivo.

Example 8

Biodistribution of Radiotherapeutic Agent ($^{131}$I-cNGEGQQc) in Mice

Fifteen normal Kunming male mice (4-6 weeks old, weight 19-21 g) were injected with 50 µl (0.48 MBq) of $^{131}$I-labeled cNGEGQQc via a tail vein respectively. At 1, 3, 6, 12, and 24 h, three animals were anesthetized and sacrificed by cervical dislocation. Whole blood was collected and organs of interest were removed and weighed. The amount of radioactivity in blood and each organ was determined and calculate the percentage of the injected dose per gram of tissue (% ID/g). Subsequently, SPECT (Millennium VG; GE Healthcare) was equipped with a low-energy, high resolution collimator. Images were acquired using energy peak centered at 364 KeV, an energy window of 20% and a 128×128 matrix at a magnification of 1.0.

The biodistribution $^{131}$I-labeled cNGEGQQc in mice was summary in Table 5. SPECT imaging showed that the kidney had the highest radioactivity levels and longer clearance among all organs in healthy mice, indicating predominant renal excretion of $^{131}$I-labeled cNGEGQQc. During the observation period, the radioactivity level in various organs gradually decreased, while the radioactivity of gastrointestinal was relatively stable. It indicated that the stability of $^{131}$I-labeled cNGEGQQc was excellent and no free $^{131}$I release in vivo. The least uptake of $^{131}$I-labeled cNGEGQQc was observed in muscles and brain.

TABLE 5

Biodistribution $^{131}$I-labeled cNGEGQQc in mice (% ID/g)

| Tissues | 1 h | 3 h | 6 h | 12 h | 24 h |
|---|---|---|---|---|---|
| liver | 0.3830 ± 0.0018 | 0.4152 ± 0.0024 | 0.1403 ± 0.0004 | 0.0829 ± 0.0007 | 0.0338 ± 0.0001 |
| spleen | 0.2034 ± 0.0008 | 0.3137 ± 0.0023 | 0.1841 ± 0.0002 | 0.0770 ± 0.0005 | 0.0384 ± 0.0001 |
| kidney | 2.4804 ± 0.0059 | 2.0763 ± 0.0072 | 0.9813 ± 0.0025 | 0.3812 ± 0.0023 | 0.2028 ± 0.0006 |
| lung | 0.3773 ± 0.0012 | 0.3896 ± 0.0021 | 0.2395 ± 0.0008 | 0.2879 ± 0.0023 | 0.0765 ± 0.0001 |
| stomach | 0.6943 ± 0.0034 | 1.2331 ± 0.0095 | 0.8734 ± 0.0035 | 0.7219 ± 0.0105 | 0.0696 ± 0.0005 |
| intestine | 0.2910 ± 0.0011 | 0.3185 ± 0.0012 | 0.1956 ± 0.0004 | 0.1354 ± 0.0009 | 0.0723 ± 0.0003 |
| muscle | 0.0800 ± 0.0002 | 0.0874 ± 0.0005 | 0.0515 ± 0.0004 | 0.0394 ± 0.0003 | 0.0206 ± 0.0001 |
| bone | 0.2420 ± 0.0005 | 0.2517 ± 0.0009 | 0.1604 ± 0.0006 | 0.0887 ± 0.0004 | 0.0702 ± 0.0001 |
| brain | 0.0279 ± 0.0007 | 0.0273 ± 0.0002 | 0.0159 ± 0.0004 | 0.0183 ± 0.0001 | 0.0170 ± 0.0001 |
| blood | 0.4297 ± 0.0019 | 0.5124 ± 0.0028 | 0.3971 ± 0.0016 | 0.1788 ± 0.0017 | 0.0644 ± 0.0002 |

Biodistribution of Radiotherapeutic Agent ($^{131}$I-cNGEGQQc) in Rabbits

Figure 15:
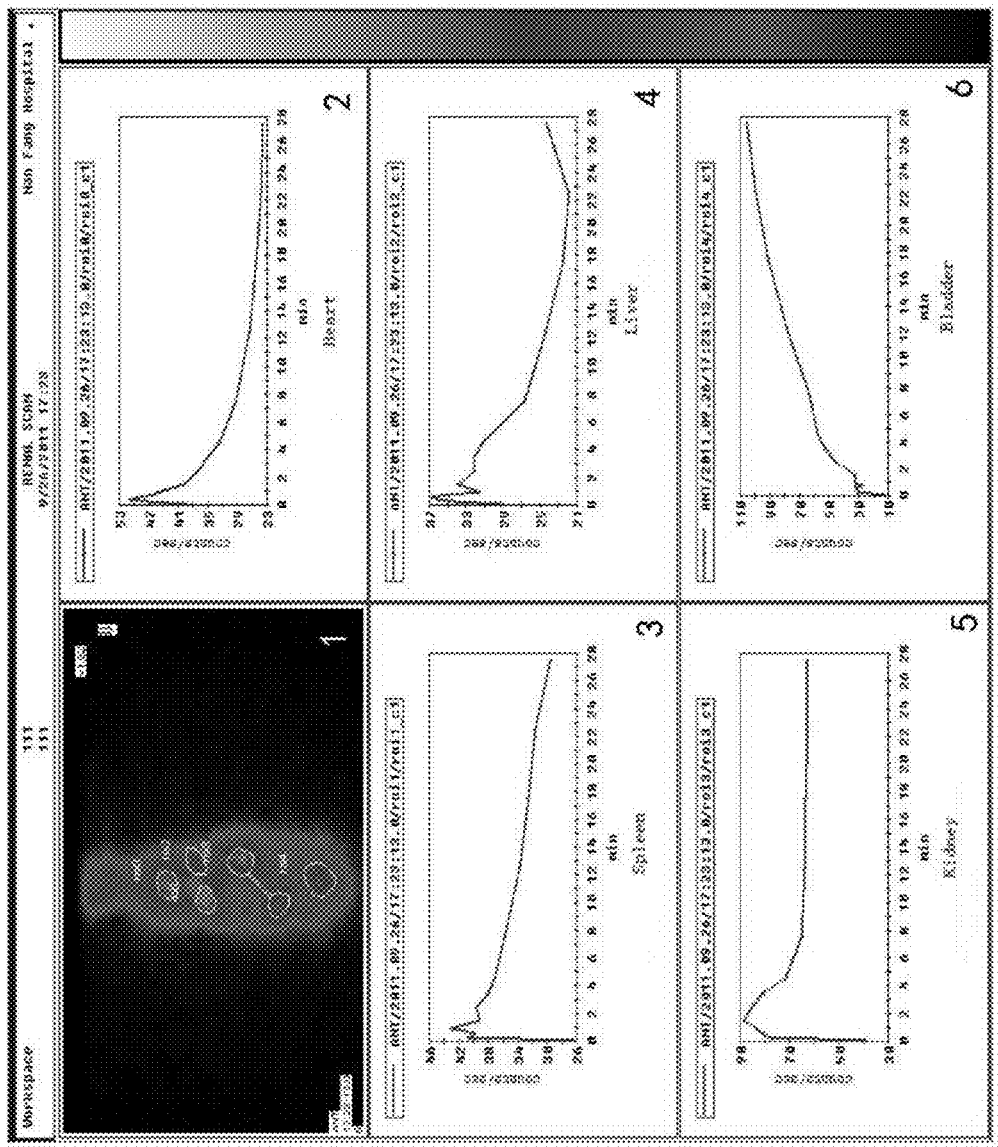
FIG. 15 shows the time-radioactivity curves of heart, liver, spleen, kidney and bladder were measured using the region-of-interest (ROI)-based analysis by injection of $^{131}$I-cNGEGQQc (1. the time-radioactivity curve from ROI analysis after dynamic recording in major organs of normal rats; 2. the time-radioactivity curve of heart; 3. the time-radioactivity curve of spleen; 4 the time-radioactivity curve of liver; 5. the time-radioactivity curve of kidney; 6. the time-radioactivity curve of bladder)
Figure 16:
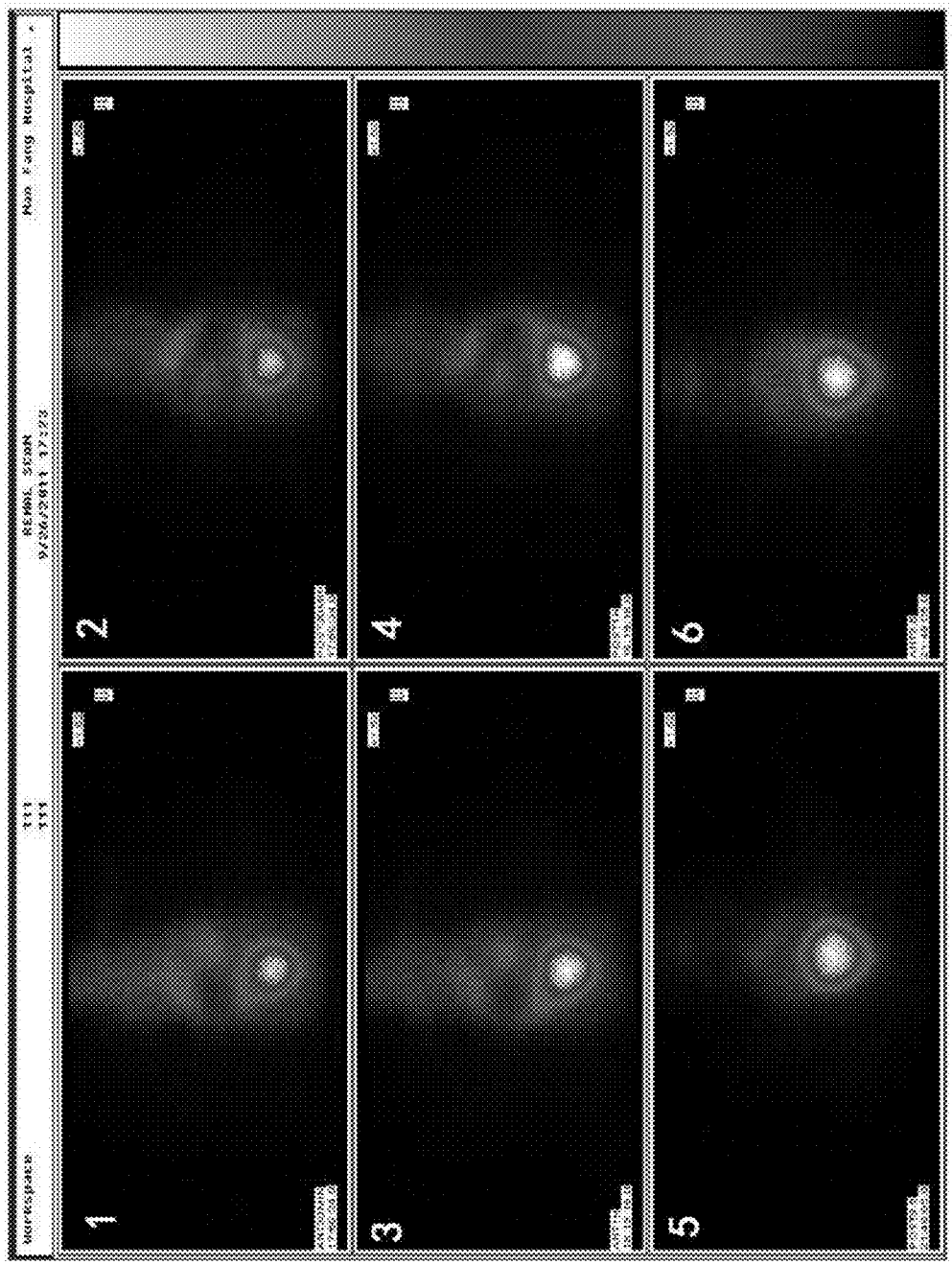
FIG. 16 shows the anterior and rear images were acquired by SPECT scanning after intravenous injection of $^{131}$I-cNGEGQQc at different time (1-2, after 30 mins injection of $^{131}$I-cNGEGQQc; 3-4, after 1 h injection of $^{131}$I-cNGEGQQc; 5-6, after 3.5 h injection of $^{131}$I-cNGEGQQc)

Two of healthy Japanese male white rabbits were fixed in supine position on a wooden experimental stage. We set SPECT collimator on the rabbit thoracic and abdominal to ensure that the whole body of rabbit was within vision field of SPECT imaging. The injectant of $^{131}$I-labeled cNGEGQQc dilution with saline water (0.5 mL/14.8 MBq) was administered through the ear vein injection. The images were obtained in two ways in order to evaluate and compare dynamic imaging with multitemporal static imaging. First, the images were acquired immediately at a rate of 1 frame/10 sec×6 after injection of the $^{131}$I-cNGEGQQc, followed by a rate of 1 frame/1 min×4 and 1 frame/5 min×5. Second, multitemporal static images of anterior and posterior were obtained following the dynamic imaging at 0.5 h, 1 h and 3.5 h after injection. The posterior dynamic images were analyzed by ROI semi-quantitatively. The time-radioactivity curves of main organs comprising precordia, liver, spleen, kidney and bladder were obtained respectively by ROI analysis (FIGS. 15-16).

Example 9

Inhibition of Lung Cancer Cell Growth by Radiotherapeutic Agent ($^{131}$I-cNGEGQQc) in Mice Animal models. Two human lung cancer cell lines comprising NCI-H1975 (adenocarcinoma) and L78 (squamous carcinoma) were maintained in RPMI 1640 (GIBCO, Mississauga, Canada) supplemented with 10% heat-inactivated calf serum (HyClone, Logan, Utah) and L-glutamine (Beyotime, Jiangsu, China) in an incubator at 37° C. with 5% $CO_2$. Cells were harvested with trypsin/EDTA, washed with PAS twice and re-suspended in free serum culture medium at a concentration of 5×10$^6$ cells/mL. The suspended cells (0.2 mL) were inoculated s.c. into the back of nude mice to establish the lung cancer models, respectively. There are twelve nude mice in each group of cancer model. Tumor growth and general states such as mental, diet and weight were monitored periodically. When tumors reached approximately 1 cm in mean diameter, the tumor bearing mice were used in therapeutic efficacy studies.

All mice received a solution of 0.2% potassium iodine orally to block uptake of free iodine-131 by the thyroid beginning from 3 days before treatment and to end of experiment. Twelve tumor bearing mice of each lung cancer cell line were randomly divided into four groups with three animals each and injected with $^{131}$I-cNGEGQQc, $^{131}$I-cNAQAEQc (negative peptide control), $^{131}$I and normal saline via a tail vein, respectively. The tumor size was measured two dimensionally on days 3, 6, 9, 12, 15, 18, 21, 24, 27 and 30 after injection, while mice weight was also determined. The tumor volume was calculated by the formula volume $V=(4/3)×π×R1×R2$, where R1 is radius 1 and R2 is radius 2 and R1<R2. Growth curves of the tumors were constructed according to these tumor volumes.

Figure 17:
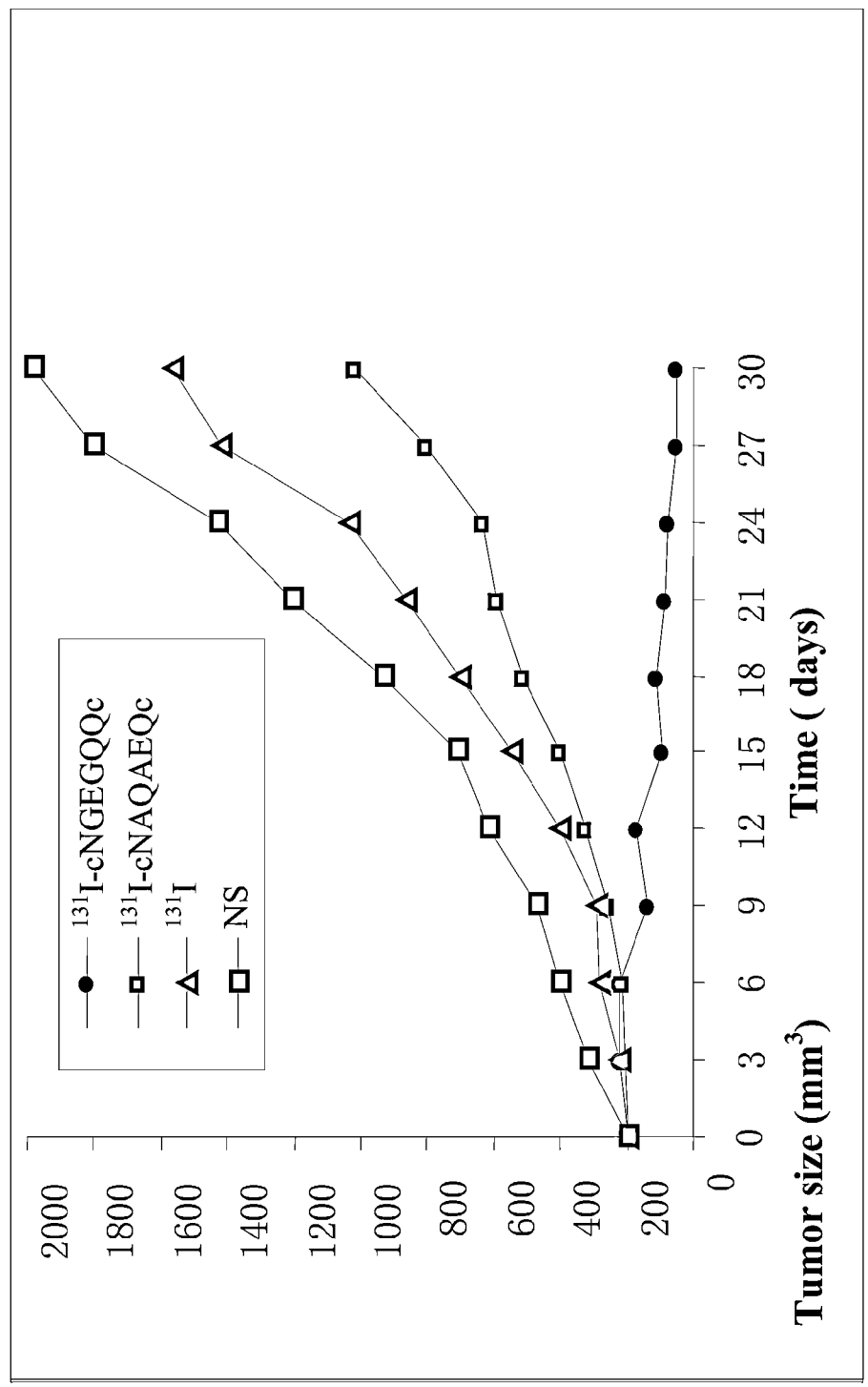
FIG. 17 shows growth curve of H1975 cells in nude mice.
Figure 18:
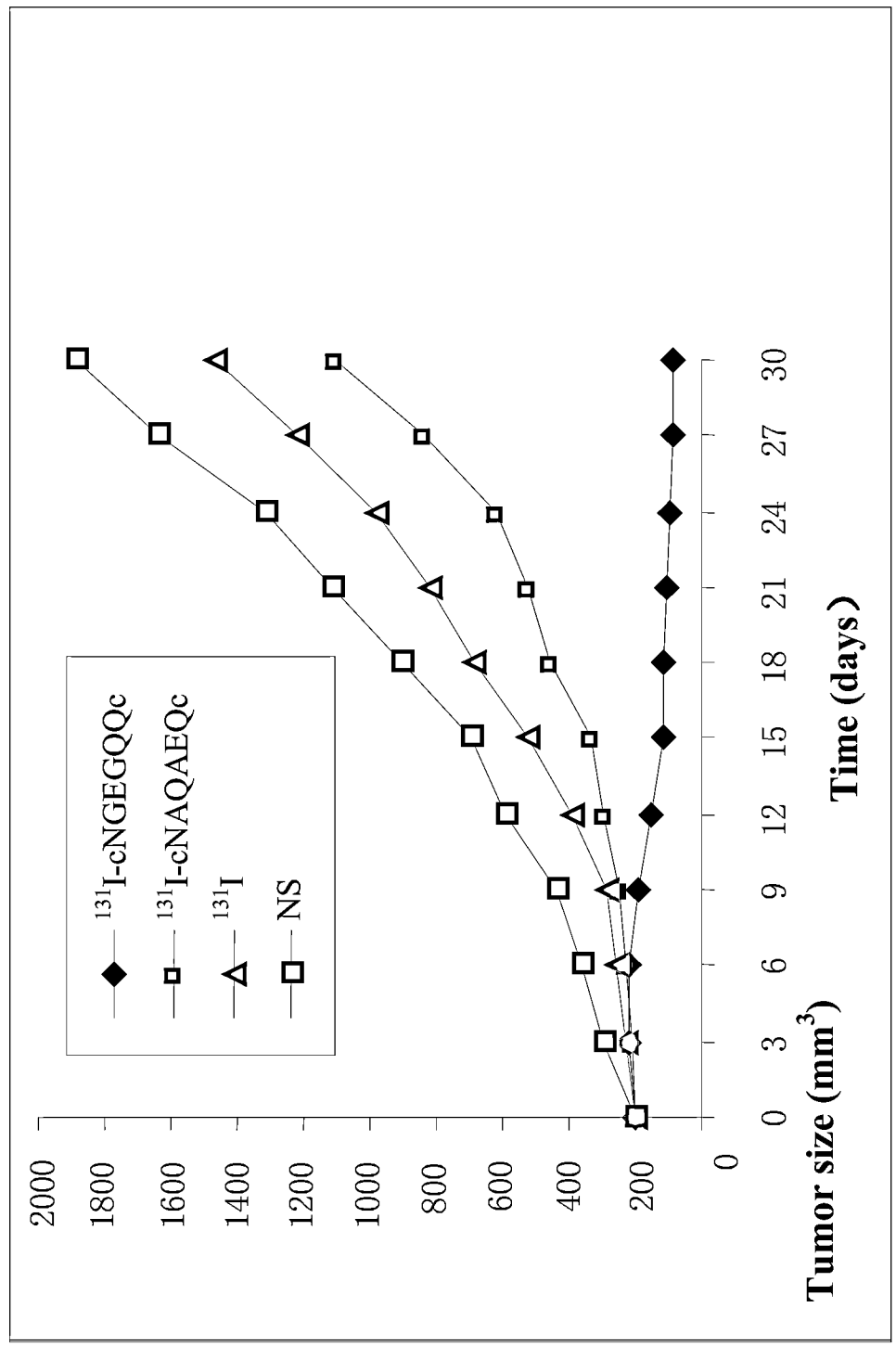
FIG. 18 shows growth curve of L78 cells in nude mice.

The tumor size of H1975 and L78 in $^{131}$I-cNGEGQQc treated groups decreased on days 7 after injection, while tumor grew continentally in the control groups (FIGS. 17-18). The median survival time of each group was as follows: 54 days in mice with $^{131}$I-cNGEGQQc; 45 days in mice with $^{131}$I-cNAQAEQc; 42 days in mice with $^{131}$I and 43 days in mice with normal saline. These results suggested that radiotherapeutic agent of the invention can significantly inhibit lung cancer growth in vivo.

Example 10

Evaluation of Toxicity of Radiotherapeutic Agent ($^{131}$I-cNGEGQQc) to Major Organs 1) Analysis of Toxicity of Radiotherapeutic Agent in Mice Bearing Lung Cancer Cells After treatment with radiotherapeutic agent for three weeks, the mice were sacrificed and the major tissues or organs such as blood, liver, kidneys, heart, lungs and spleen were removed completely. A routine blood test was performed using an automatic hematology analyzer to measure the following parameters: white blood cell (WBC), red blood cell (RBC) and platelet (PLT) count. Clinical biochemicals parameters measured with an automated biochemical analyzer were aspartate transferase (AST), alanine transferase (ALT), blood urea nitrogen (BUN) and creatinine (CRE). Histopathological and ultrastructural observations were performed on the preserved organs and tissues stated above.

The hematological analysis showed no significant changes of RBC, WBC and PLT in the radiotherapeutic agent treatment groups compared to the normal saline groups. The leukocyte count showed decrease between the control and $^{131}$I-cNAQAEQc or $^{131}$I groups. The data from the serum biochemical examinations demonstrated that there were no statistically significant differences of AST, ALT, BUN and CRE in either the control or treated group (P<0.05) (Table 6). The organs comprising liver, kidneys, heart and lungs were carefully examined. No histopathological and ultrastructural changes were observed in the organs of the control or treated group.

2) Analysis of Toxicity of Radiotherapeutic Agent in Normal Rabbits

TABLE 6

Effect of 131I-cNGEGQQc on blood cell and liver and kidney function in mice bearing lung cancer (24 h)

| Groups | Hematological analysis | | |
|---|---|---|---|
| | RBC(T/L) | WBC(G/L) | PLT(G/L) |
| $^{131}$I-cNGEGQQc | 8.1 ± 0.4 | 16.5 ± 0.5 | 1024.7 ± 39.0 |
| $^{131}$I-cNAQAEQc | 7.8 ± 0.3 | 14.4 ± 1.5* | 974.7 ± 31.2 |
| $^{131}$I | 7.8 ± 0.2 | 13.6 ± 0.7* | 991.2 ± 52.5 |
| Normal saline | 8.4 ± 0.5 | 17.8 ± 1.2 | 1143.8 ± 33.9 |
| P value | >0.05 | >0.05 | >0.05 |

| Groups | Biochemicals analysis | | | |
|---|---|---|---|---|
| | ALT(U/L) | AST(U/L) | BUN (mmol/L) | CRE (μmol/L) |
| $^{131}$I-cNGEGQQc | 59.3 ± 4.8 | 173.6 ± 2.8 | 9.3 ± 0.6 | 33.4 ± 3.0 |
| $^{131}$I-cNAQAEQc | 62.6 ± 4.8 | 181.5 ± 5.1 | 9.8 ± 1.4 | 39.2 ± 2.5 |
| $^{131}$I | 60.7 ± 7.8 | 171.7 ± 0.8 | 9.4 ± 1.3 | 42.7 ± 3.8 |
| Normal saline | 66.0 ± 4.7 | 150.0 ± 2.7 | 8.2 ± 0.7 | 41.0 ± 3.3 |
| P value | >0.05 | >0.05 | >0.05 | >0.05 |

In relation to the hematological parameters, similar data were observed for the values of the control group; the effects were considered to be of no toxicological significance (p>0.05).

Six healthy rabbit were randomly divided into two groups with three animals each and injected with $^{131}$I-cNGEGQQc and normal saline via a tail vein, respectively. Body temperature of each rabbit was measured at 15 min before injection and at 1 h, 12 h and 24 h after injection. The temperature range of each rabbit at different time point was as follow: 38.9-39.3° C. before injection; 38.7-39.2° C. at 1 h after injection; 39.1-39.6° C. at 12 h after injection; 38.9-39.1° C. at 24 h after injection. The largest temperature variance of each animal was below 0.7° C. during 24 h and below 1.5° C. in three tests. The blood samples were drawn from the ear vein of the rabbits for testing the count of blood cell (comprising RBC, WBC and PLT) and liver function (AST and ALT) and kidney function (CRE and BUN). The hematological analysis, liver and kidney function at three time-points were listed in Table 7. Based on the analysis results of the above-mentioned parameters, no significant differences were found between the treatment and the control group (P<0.05), except for a decrease of PLT at 24 h after treatment. No significant differences were also found in respiratory, autonomic and central nervous system and behavior pattern. These observations clearly suggest there is no toxicity of $^{131}$I-cNGEGQQc to major organs comprising lungs, liver, kidneys and heart.

TABLE 7

Effect of $^{131}$I-cNGEGQQc on blood cell and liver and kidney function

| Groups | Hematological analysis | | |
|---|---|---|---|
| | RBC(T/L) | WBC(G/L) | PLT(G/L) |
| Before treatment | 4.8 ± 0.3 | 11.3 ± 0.5 | 343.7 ± 5.2 |
| After treatment(24 h) | 5.4 ± 0.5 | 9.6 ± 0.3 | 222.7 ± 5.3* |
| After treatment(3 m) | 5.2 ± 0.2 | 12.7 ± 1.7 | 320.7 ± 49.6 |
| P value | >0.05 | >0.05 | <0.05 |

| Groups | Biochemicals analysis | | | |
|---|---|---|---|---|
| | ALT(U/L) | AST(U/L) | BUN (mmol/L) | CRE (μmol/L) |
| Before treatment | 48.7 ± 1.8 | 14.3 ± 2.9 | 6.0 ± 0.5 | 89.3 ± 4.3 |
| After treatment(24 h) | 60.5 ± 10.3 | 22.1 ± 6.8 | 8.6 ± 0.3 | 97.7 ± 4.9 |
| After treatment(3 m) | 49.4 ± 3.9 | 22.6 ± 6.3 | 9.9 ± 5.6 | 101.3 ± 8.4 |
| P value | >0.05 | >0.05 | >0.05 | >0.05 |

The examples described above are preferred embodiments of the present invention. For the skilled person in the field, any apparent changes in the invention without departing from the spirit and scope for improvement should be considered part of the present invention.

The invention claimed is:

1. A peptide comprising 8 amino acids with a sequence of cNGEGQQc (SEQ ID NO. 1), wherein c represents d-cysteine (Cys), N represents L-Asparagine (Asn), G represents L-Glycine (Gly), E represents L-Glutamic acid (Glu), and Q represents L-Glutamine (Gln).

2. The peptide of claim 1, wherein the peptide accumulates within the H1975 adenocarcinoma or L78 squamous carcinoma xenograft tumor.

3. A method of preparing a molecular imaging probe for a non-small cell lung cancer, the method comprising labeling the peptide of claim 1 with an imaging agent, wherein the imaging agent is $^{99m}$Tc, $^{111}$In, $^{18}$F-FDG, $^{68}$Ga, or $^{64}$Cu.

4. A method of preparing a radiotherapeutic agent for a non-small cell lung cancer, the method comprising labeling the peptide of claim 1 with a radiotherapeutic isotope, wherein the radiotherapeutic isotope is $^{131}$I or $^{125}$I.

* * * * *